(12) United States Patent
Kim et al.

(10) Patent No.: US 7,094,368 B2
(45) Date of Patent: Aug. 22, 2006

(54) PYRANO-QUINOLINES, PYRANO-QUINOLINONES, COMBINATIONS THEREOF, PHOTOCHROMIC COMPOSITIONS AND ARTICLES

(75) Inventors: Beon-Kyu Kim, Gibsonia, PA (US); Anil Kumar, Pittsburgh, PA (US); Barry Van Gemert, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 46 days.

(21) Appl. No.: 10/732,008

(22) Filed: Dec. 10, 2003

(65) Prior Publication Data

US 2005/0127336 A1    Jun. 16, 2005

(51) Int. Cl.
*G02B 5/23* (2006.01)
*C08K 5/1545* (2006.01)
*G02C 7/10* (2006.01)

(52) U.S. Cl. .................. 252/586; 351/163; 524/110; 544/150; 544/375

(58) Field of Classification Search ................. 252/586
See application file for complete search history.

(56) References Cited

U.S. PATENT DOCUMENTS

| | | | |
|---|---|---|---|
| 3,361,706 A | 1/1968 | Smith et al. | 260/39 |
| 4,166,043 A | 8/1979 | Uhlmann et al. | 252/300 |
| 4,360,653 A | 11/1982 | Stevens et al. | 526/301 |
| 4,367,170 A | 1/1983 | Uhlmann et al. | 252/586 |
| 4,556,605 A | 12/1985 | Mogami et al. | 428/331 |
| 4,720,356 A | 1/1988 | Chu | 252/586 |
| 4,756,973 A | 7/1988 | Sakagami et al. | 428/412 |
| 4,798,745 A | 1/1989 | Martz et al. | 427/407.1 |
| 4,798,746 A | 1/1989 | Claar et al. | 427/407.1 |
| 4,873,029 A | 10/1989 | Blum | 264/1.3 |
| 4,889,413 A | 12/1989 | Ormsby et al. | 350/354 |
| 4,931,220 A | 6/1990 | Haynes et al. | 252/586 |
| 4,994,208 A | 2/1991 | McBain et al. | 252/586 |
| 5,106,998 A | 4/1992 | Tanaka et al. | 549/331 |
| 5,166,345 A | 11/1992 | Akashi et al. | 544/71 |
| 5,200,483 A | 4/1993 | Selvig | 526/301 |
| 5,236,958 A | 8/1993 | Miyashita | 518/121 |
| 5,239,012 A | 8/1993 | McEntire et al. | 525/327.7 |
| 5,252,742 A | 10/1993 | Miyashita | 548/121 |
| 5,274,132 A | 12/1993 | VanGemert | 549/389 |
| 5,349,065 A | 9/1994 | Tanaka et al. | 546/15 |
| 5,359,085 A | 10/1994 | Iwamoto et al. | 548/468 |
| 5,373,033 A | 12/1994 | Toh et al. | 522/96 |
| 5,391,327 A | 2/1995 | Ligas et al. | 252/586 |
| 5,451,344 A | 9/1995 | Knowles et al. | 252/586 |
| 5,458,814 A | 10/1995 | Kumar et al. | 252/586 |
| 5,475,074 A | 12/1995 | Matsuoka et al. | 526/336 |
| 5,488,119 A | 1/1996 | Fischer-Reimann et al. | 552/201 |
| 5,527,911 A | 6/1996 | Guglielmetti et al. | 544/250 |
| 5,608,065 A | 3/1997 | Melzig | 546/15 |
| 5,618,586 A | 4/1997 | Swarup et al. | 427/407.1 |
| 5,637,709 A | 6/1997 | Melzig | 544/231 |
| 5,645,767 A | 7/1997 | Van Gemert | 252/586 |
| 5,658,501 A | 8/1997 | Kumar et al. | 252/586 |
| 5,753,146 A | 5/1998 | Van Gemert et al. | 252/586 |
| 5,770,115 A | 6/1998 | Misura | 252/586 |
| 5,821,287 A | 10/1998 | Hu et al. | 524/89 |
| 5,965,630 A | 10/1999 | Imafuku et al. | 523/106 |
| 5,965,631 A | 10/1999 | Nicolson et al. | 523/106 |
| 6,025,026 A | 2/2000 | Smith et al. | 427/316 |
| 6,060,001 A | 5/2000 | Welch et al. | 252/586 |
| 6,113,814 A | 9/2000 | Van Gemert et al. | 252/586 |
| 6,150,430 A | 11/2000 | Walters et al. | 522/79 |
| 6,153,126 A | 11/2000 | Kumar | 252/586 |
| 6,187,444 B1 | 2/2001 | Bowles, III et al. | 428/423.1 |
| 6,268,055 B1 | 7/2001 | Walters et al. | 428/413 |
| 6,296,785 B1 | 10/2001 | Nelson et al. | 252/586 |
| 6,348,604 B1 | 2/2002 | Nelson et al. | 549/389 |
| 6,353,102 B1 | 3/2002 | Kumar | 544/60 |
| 6,432,544 B1 | 8/2002 | Stewart et al. | 428/424.2 |
| 6,506,488 B1 | 1/2003 | Stewart et al. | 428/332 |
| 6,555,028 B1 | 4/2003 | Walters et al. | 252/586 |

FOREIGN PATENT DOCUMENTS

JP    02-311479    12/1990

(Continued)

OTHER PUBLICATIONS

Nair, Vijay et al., Diels-Alder trapping of 3-metylenequinolin-2,4-dione: a facile synthesis of Pyranoquinolinones and spiroquinolinediones, Tetrahedron, 57, 2001, 7711-7717.*

(Continued)

*Primary Examiner*—Randy Gulakowski
*Assistant Examiner*—Timothy J. Kugel
(74) *Attorney, Agent, or Firm*—Linda Pingitore; Frank P. Mallak

(57) ABSTRACT

Described are compositions of at least one material represented by a pyrano[3,2-c]quinoline structure, a pyrano[3,2-c]quinolinone structure or mixtures thereof. The pyrano[3,2-c]quinoline structure is characterized by having a nitrogen atom at the 6-position ring atom and an oxy-substituent at the 5-position ring atom. The pyrano[3,2-c]quinolinone structure is characterized by having a substituted nitrogen atom at the 6-position ring atom and an oxo-substituent at the 5-position ring atom, the nitrogen atom substituents being hydrogen, aliphatic substituents, cycloaliphatic substituents, aromatic substituents, heteroaromatic substituents or a combination thereof. Both of the pyrano[3,2-c]quinoline and pyrano[3,2-c]quinolinone structures are characterized by having two substituents at the 2-position ring atom. Also described are photochromic articles that contain or that have coatings or films containing at least one of the novel compositions or combinations thereof with other photochromic materials.

5 Claims, No Drawings

FOREIGN PATENT DOCUMENTS

| JP | 06-199827 | 7/1994 |
|---|---|---|
| JP | 07-258245 | 10/1995 |
| JP | 08-295690 | 11/1996 |
| WO | WO 97/05213 | 2/1997 |
| WO | WO 98/04937 | 5/1998 |
| WO | WO 01/02449 A2 | 1/2001 |

OTHER PUBLICATIONS

Manikandan, S. et al., Competition between two intermolecular domino Knoevenagel hetero Diels-Alder reactions: a new entry into novel pyranoquinolinone derivatives, Tetrahedron, 58, 2002, 8957-8962.*

Becker, Ralph et al., Photochromism of Synthetic and Naturally Occurring 2H-Chromenes and 2H-Pyrans, Journal of the American Chemical Society, 88:24, Dec. 20, 1966, 5931-5933.*

Becker, Ralph et al., Vibronic Quantum Effects in Fluorescence and Photochemistry. Competition between Vibrational Relaxation and Photochemistry and Consequences for Photochemical Control, Journal of the American Chemical Society, 1999, 121, 2104-2109.*

*Hawley's Condensed Chemical Directory*, Thirteenth edition, 1997, John Wiley & Sons, pp. 901-902.

*J. Am. Chem. Soc.*, S.A. Glickman, et al. (1945), vol. 67, p. 1017.

N.D. Harris, Synthesis (1976), pp. 286-287.

*Friedel-Crafts and Related Reactions*, George A. Olah, Interscience Publishers, 1964, vol. 3, Chapter XXXI (Aromatic Ketone Syntheses).

"Regioselective Friedel-Crafts Acylation of 1,2,3,4-Tetrahydroquinoline and Related Nitrogen Heterocycles: Effects of NH Protective Groups and Ring Size" by Ishihara, Yugi, et al., J. Chem. Soc. Perkin Trans. 1, pp. 3401 to 3406, 1992.

The Synthesis of Aldehydes from Dihydro-1,3-oxazines by A.I. Meyers, et al., *J. Org. Chem* (1973), vol. 38, p. 36.

"Photochromism," *Techniques of Chemistry*, vol. III, Chapter 3, Glenn H. Brown, Editor, John Wiley and Sons, Inc., New York 1971.

Kirk-Othmer *Encyclopedia of Chemical Technology*, Fourth Edition, vol. 6, pp. 669 to 760.

*Ullmann's Encyclopedia of Industrial Chemistry*, Fifth Edition, 1992, vol. A21, pp. 665 to 716.

ASTM F-735-94 "Standard Test Method for Abrasion Resistance of Transparent Plastics and Coatings Using the Oscillating Sand Method."

"Quinolinone Alkaloids From An Agathosma Species*", W.E. Campbell; B. Davidowitz; G.E. Jackson; *Phytochemistry*, vol. 29, No. 4, 1990, pp. 1303-1306.

"Total Syntheses of Pyranoquinoline Alkaloids: Simulenoline, Huajiaosimuline, and (±)-7-Demethoxyzanthodioline", M.J. McLaughlin; R. P. Hsung, *Journal of Organic Chemistry*, 2001, pp. 1049-1-53.

"Pyranoquinoline Alkaloids From Zanthoxylum Simulans", I.S. Chen, I.W. Tsai, C.M. Teng, J.J. Chen, Y.L.Chang, F.N. Ko, M.C. Lu, J.M.Puzzuto, *Phytochemistry*, vol. 46, No. 3, pp. 525-529.

"Angular Methoxy-Substituted Furo- and Pyranoquinolines as Blockers of the Voltage-Gated Potassium Channel Kvl.3", K. Butenschon, K. Moller, W. Hansel, *Journal of Medical Chemistry*, 2001, pp. 1249-1256.

* cited by examiner

PYRANO-QUINOLINES, PYRANO-QUINOLINONES, COMBINATIONS THEREOF, PHOTOCHROMIC COMPOSITIONS AND ARTICLES

BACKGROUND OF THE INVENTION

The present invention relates to novel chromene materials having a nitrogen heteroatom. More particularly, this invention relates to materials of pyrano[3,2-c]quinoline structure and/or of pyrano[3,2-c]quinolinone structure and to compositions and photochromic articles comprising photochromic materials of these structures. When exposed to light radiation containing ultraviolet rays, such as the ultraviolet radiation in sunlight or the light of a mercury lamp, many photochromic materials exhibit a reversible change in color. When the ultraviolet radiation is discontinued, such a photochromic material will return to its original color or colorless state.

Various classes of photochromic materials have been synthesized and suggested for use in applications in which a sunlight-induced reversible color change is desired. Although polycyclic aromatic hydrocarbon materials having a nitrogen heteroatom are known, there is a need for such materials that can demonstrate a range of photochromic performance properties.

DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

In one non-limiting embodiment of the present invention, there is provided a composition comprising at least one material represented by a pyrano[3,2-c]quinoline structure, a pyrano[3,2-c]quinolinone structure or by mixtures thereof, which includes materials represented by both of the structures. In another non-limiting embodiment, the pyrano[3,2-c]quinoline structure comprises a nitrogen atom at the 6-position ring atom and an oxy-substituent at the 5-position ring atom; and the pyrano[3,2-c]quinolinone structure comprises a substituted nitrogen atom at the 6-position ring atom and an oxo-substituent at the 5-position ring atom, the nitrogen substituents being chosen from hydrogen, aliphatic substituents, cycloaliphatic substitutents, aromatic substituents, heteroaromatic substituents or a combination thereof. In a further non-limiting embodiment, the 2-position ring atom of each of the pyrano[3,2-c]quinoline and pyrano[3, 2-c]quinolinone structures comprises two substituents, each independently chosen from aliphatic substituents, cycloaliphatic substituents, aromatic substituents, heteroaromatic substituents or a combination thereof, provided that both substituents at the 2-position ring atom are not aliphatic. In an alternative non-limiting embodiment, the two substituents at the 2-position ring atom combine to form a spirocyclic group, provided that said spirocyclic group is not norbornylidene or bicyclo[3.3.1]9-nonylidene. The aforementioned ring atoms being numbered according to the International Union of Pure and Applied Chemistry rules of nomenclature starting with the 1-position ring atom being the oxygen atom of the pyran ring and numbering counterclockwise therefrom.

In a further non-limiting embodiment, the present invention includes a photochromic article comprising an at least partially cured polymeric organic host and at least a photochromic amount of a composition comprising at least one material represented by a pyrano[3,2-c]quinoline structure, a pyrano[3,2-c]quinolinone structure or by a mixture thereof. The phrase "an at least partially cured organic polymeric host" refers to a polymeric material in which the curable or cross-linkable components are at least partially cured, crosslinked and/or reacted. In alternate non-limiting embodiments of the present invention, the degree of reacted components, can vary widely, e.g., from 5% to 100% of all the possible curable, crosslinkable and/or reactable components. The phrase "photochromic amount" refers to an amount used to produce a photochromic effect discernible to the naked eye upon activation.

In another non-limiting embodiment, the present invention includes a photochromic article comprising a substrate and an at least partial coating of a photochromic polymeric coating comprising a film forming polymer and at least a photochromic amount of a composition comprising at least one material represented by a pyrano[3,2-c]quinoline structure, a pyrano[3,2-c]quinolinone structure or by a mixture thereof. The phrase "an at least partial coating" means an amount of coating covering from a portion to the complete surface of the substrate.

In non-limiting embodiments, the materials of the present invention can be represented by the following graphic formulae I and/or I' in which the letters a through n represent the ring sides of the materials, and the numbers 1 through 10 represent the numbers of the ring atoms of the materials:

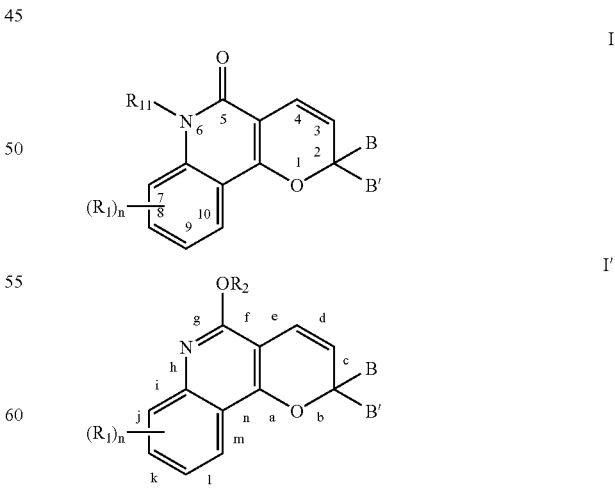

In a further non-limiting embodiment, the present invention includes a composition comprising at least one material represented by at least one of the following graphic formulae or mixtures thereof, which includes materials represented by both of the graphic formulae I and I'.

In one non-limiting embodiment, $R_{11}$ of graphic formula I is chosen from:

(i) hydrogen, $C_1$–$C_{12}$ alkyl, e.g., substituents including methyl, ethyl, propyl, isopropyl, butyl, t-butyl, pentyl, hexyl, heptyl, octyl, nonyl, decyl, undecyl and dodecyl, $C_1$–$C_{12}$ acyl, phenyl($C_1$–$C_{12}$)alkyl, mono($C_1$–$C_{12}$) alkyl substituted phenyl($C_1$–$C_{12}$)alkyl, mono($C_1$–$C_{12}$) alkoxy substituted phenyl($C_1$–$C_{12}$)alkyl, $C_1$–$C_{12}$ alkoxy($C_1$–$C_{12}$)alkyl, $C_3$–$C_7$ cycloalkyl, mono ($C_1$–$C_{12}$)alkyl substituted $C_3$–$C_7$ cycloalkyl, $C_1$–$C_{12}$ haloalkyl, allyl, benzoyl, mono-substituted benzoyl, naphthoyl or mono-substituted naphthoyl; each of said benzoyl and naphthoyl substituents being independently chosen from $C_1$–$C_{12}$ alkyl or $C_1$–$C_{12}$ alkoxy;

(ii) —CH($R_3$)Q, wherein $R_3$ being chosen from hydrogen or $C_1$—$C_{12}$ alkyl and Q being chosen from —CN, —CF$_3$, or —COOR$_4$ and $R_4$ being chosen from hydrogen or $C_1$–$C_{12}$ alkyl; or (iii) —C(O)V, wherein V being chosen from hydrogen, $C_1$–$C_{12}$ alkoxy, phenoxy, mono- or di-($C_1$–$C_{12}$)alkyl substituted phenoxy, mono- or di-($C_1$–$C_{12}$)alkoxy substituted phenoxy, an unsubstituted, mono- or di-substituted aryl group, amino, mono($C_1$–$C_{12}$)alkylamino, di($C_1$–$C_{12}$)alkylamino, phenylamino, mono- or di-($C_1$–$C_{12}$)alkyl substituted phenylamino, or mono- or di-($C_1$–$C_{12}$)alkoxy substituted phenylamino; each of said aryl group substituents being independently chosen from $C_1$–$C_{12}$ alkyl or $C_1$–$C_{12}$ alkoxy.

In another non-limiting embodiment, each $R_1$ of graphic formulae I and I' is independently chosen from:

(i) hydrogen, hydroxy, $C_1$–$C_{12}$ alkyl, $C_2$–$C_{12}$ alkylidene, $C_2$–$C_{12}$ alkylidyne, vinyl, $C_3$–$C_7$ cycloalkyl, $C_1$–$C_{12}$ haloalkyl, allyl, benzyl, mono-substituted benzyl, halogen or the group, —C(O)W, wherein W being hydroxy, $C_1$–$C_{12}$ alkyl, $C_1$–$C_{12}$ alkoxy, phenyl, mono-substituted phenyl, amino, mono($C_1$–$C_{12}$)alkylamino, di($C_1$–$C_{12}$) alkylamino; said amino substituents being $C_1$–$C_{12}$ alkyl, phenyl, benzyl or naphthyl; each of said benzyl and phenyl substituents being $C_1$–$C_{12}$ alkyl or $C_1$–$C_{12}$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (ii) being chosen independently for each occurrence from halogen, $C_1$–$C_{12}$ alkyl or $C_1$–$C_{12}$ alkoxy;

(iii) a mono-substituted phenyl, said phenyl having a substituent located at the para position being —(CH$_2$)$_t$— or —O—(CH$_2$)$_t$—, wherein t is an integer chosen from 1, 2, 3, 4, 5 or 6; said substituent being connected to an aryl group on another photochromic material;

(iv) —OR$_2$, R$_2$ being chosen from R$_{11}$, tri($C_1$–$C_{12}$)alkylsilyl, tri($C_1$–$C_{12}$)alkoxysilyl, di($C_1$–$C_{12}$)alkyl ($C_1$–$C_{12}$ alkoxy)silyl or di($C_1$–$C_{12}$)alkoxy($C_1$–$C_{12}$ alkyl)silyl;

(v) —CH(Q')$_2$, Q' being chosen from —CN or —COOR$_6$ and R$_6$ being chosen from hydrogen, $C_1$–$C_{12}$ alkyl, phenyl($C_1$–$C_{12}$)alkyl, mono($C_1$–$C_{12}$)alkyl substituted phenyl($C_1$–$C_{12}$)alkyl, mono($C_1$–$C_{12}$)alkoxysubstituted phenyl($C_1$–$C_{12}$)alkyl or an unsubstituted, mono- or di-substituted aryl group; each of said aryl group substituents being independently chosen from $C_1$–$C_{12}$ alkyl or $C_1$–$C_{12}$ alkoxy;

(vi) —CH(R$_7$)G, R$_7$ being chosen from hydrogen, $C_1$–$C_{12}$ alkyl or an unsubstituted, mono- or di-substituted aryl group and G being chosen from —COOR$_5$, —COR$_8$ or —CH$_2$OR$_9$; wherein R$_8$ being chosen from hydrogen, $C_1$–$C_{12}$ alkyl, an unsubstituted, mono- or di-substituted aryl group, amino, mono($C_1$–$C_{12}$)alkylamino, di($C_1$–$C_{12}$)alkylamino, phenylamino, mono- or di-($C_1$–$C_{12}$)alkyl substituted phenylamino, mono- or di-($C_1$–$C_{12}$)alkoxy substituted phenylamino, diphenylamino, mono- or di($C_1$–$C_{12}$)alkyl substituted diphenylamino, mono- or di($C_1$–$C_{12}$)alkoxy substituted diphenylamino, morpholino or piperidino R$_9$ being chosen from hydrogen, —C(O)R$_6$, $C_1$–$C_{12}$ alkyl, $C_1$–$C_{12}$ alkoxy($C_1$–$C_{12}$)alkyl, phenyl($C_1$–$C_{12}$)alkyl, mono($C_1$–$C_{12}$)alkoxy substituted phenyl($C_1$–$C_{12}$)alkyl or an unsubstituted, mono- or di-substituted aryl group, each of said aryl group substituents being independently chosen from $C_1$–$C_{12}$ alkyl or $C_1$–$C_{12}$ alkoxy;

(vii) the group T represented by the formula:

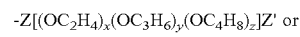

wherein -Z is chosen from —C(O)— or —CH$_2$—, Z' being chosen from $C_1$–$C_{12}$ alkoxy or a polymerizable group, x, y and z are each a number between 0 and 50, and the sum of x, y and z is between 2 and 50.

In alternate non-limiting embodiments of the aforementioned group T formula, the group, —(OC$_2$H$_4$)$_x$—, can represent poly(ethylene oxide); —(OC$_3$H$_6$)$_y$—, can represent poly(propylene oxide); and, —(OC$_4$H$_8$)$_z$—, can represent poly(butylene oxide). When used in combination, the poly(ethylene oxide), poly(propylene oxide) and poly(butylene oxide) groups of T can be in a random or block order within the T moiety. The letters x, y and z are each a number between 0 and 50 and the sum of x, y and z is between 2 and 50. The sum of x, y and z can be any number that falls within the range of 2 to 50, e.g., 2, 3, 4 . . . 50. This sum may also range from any lower number to any higher number within the range of 2 to 50, e.g., 6 to 50, 31 to 50. The numbers for x, y, and z are average values and can be partial numbers, e.g., 9.5.

In one non-limiting embodiment, polymerization of the materials having polymerizable substituents, e.g., substituents represented by group T formulae, can occur by mechanisms described in the definition of "polymerization" in *Hawley's Condensed Chemical Dictionary* Thirteenth Edition, 1997, John Wiley & Sons, pages 901–902. In this reference, it is stated that "The polymerization reaction occurs spontaneously in nature; industrially it is performed by subjecting unsaturated or otherwise reactive substances to conditions that will bring about combination." The mechanisms described by which polymerization occurs include by "addition", in which free radicals are the initiating agents that react with the double bond of the monomer by adding to it on one side at the same time producing a new free electron on the other side; by "condensation", involving the splitting out of water molecules by two reacting monomers; and by so-called "oxidative coupling".

Non-limiting examples of the polymerizable groups of the group T formulae are hydroxy, (meth)acryloxy, 2-(meth-acryloxy)ethylcarbamyl, or epoxy, e.g., oxiranylmethyl. When there are 2 or more polymerizable groups on the material, they can be the same or different.

In further non-limiting embodiments, each R$_1$ of graphic formulae I and I' is independently chosen from:

(viii) —SR$_{10}$, R$_{10}$ being chosen from C$_1$–C$_{12}$ alkyl, aryl, mono- or di-substituted aryl, and each of said aryl substituents being chosen independently from C$_1$–C$_{12}$ alkyl, C$_1$–C$_{12}$ alkoxy or halogen;

(ix) —N(R$_{11}$)R$_{12}$, wherein R$_{12}$ is the same as R$_{11}$ described herein before;

(x) a nitrogen containing ring represented by the following graphic formula IIA:

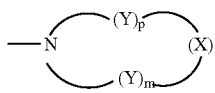

IIA wherein each Y being independently chosen for each occurrence from —CH$_2$—, —CH(R$_{13}$)—, —C(R$_{13}$)(R$_{13}$)—, —CH(aryl)-, —C(aryl)$_2$— or —C(R$_{13}$)(aryl)-; X being —Y—, —O—, —S—, —S(O)—, —S(O$_2$)—, —NH—, —NR$_{13}$— or —N-aryl; R$_{13}$ being C$_1$–C$_{12}$ alkyl; m is an integer chosen from 1, 2 or 3 and p is an integer chosen from 0, 1, 2 or 3; provided that when p is 0, X is Y;

(xi) a group represented by one of the following graphic formulae IIB or IIC:

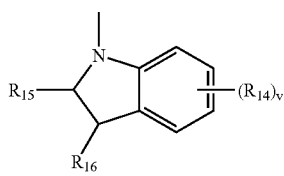

IIB

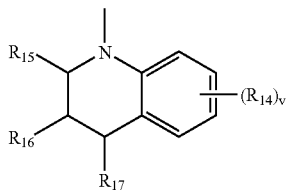

IIC wherein R$_{15}$, R$_{16}$ and R$_{17}$ are each chosen independently for each occurrence in each formula from hydrogen, C$_1$–C$_{12}$ alkyl, phenyl or naphthyl; or the groups R$_{15}$ and R$_{16}$ together form a ring of 5 to 8 carbon atoms, R$_{14}$ being chosen independently for each occurrence from C$_1$–C$_{12}$ alkyl, C$_1$–C$_{12}$ alkoxy, or halogen and v is an integer chosen from 0, 1 or 2;

(xii) unsubstituted, mono- or di- substituted C$_4$–C$_{18}$ spirobicyclic amine;

(xiii) unsubstituted, mono- or di- substituted C$_4$–C$_{18}$ spirotricyclic amine; said substituents for (xii) and (xiii) being independently chosen for each occurrence from aryl, C$_1$–C$_{12}$ alkyl, C$_1$–C$_{12}$ alkoxy or phenyl (C$_1$–C$_{12}$) alkyl.

Non-limiting examples of mono- or di-substituted bicyclicamines include: 2-azabicyclo[2.2.1]hept-2-yl; 3-azabicyclo[3.2.1]oct-3-yl; 2-azabicyclo[2.2.2]oct-2-yl; 6-azabicyclo[3.2.2]nonan-6-yl and tricyclicamines include: 2-azatricyclo[3.3.1.1(3,7)]decan-2-yl; 4-benzyl-2-azatricyclo[3.3.1.1(3,7)]decan-2-yl;4-methoxy-6-methyl-2-azatricyclo[3.3.1.1(3,7)]decan-2-yl;4-azatricyclo[4.3.1.1(3,8)]undecan-4-yl; and 7-methyl-4-azatricyclo[4.3.1.1(3,8)] undecan-4-yl.

In an alternative non-limiting embodiment (xiv) adjacent R$_1$ substituents come together to form one of the following graphic formulae IID, IIE, or IIF:

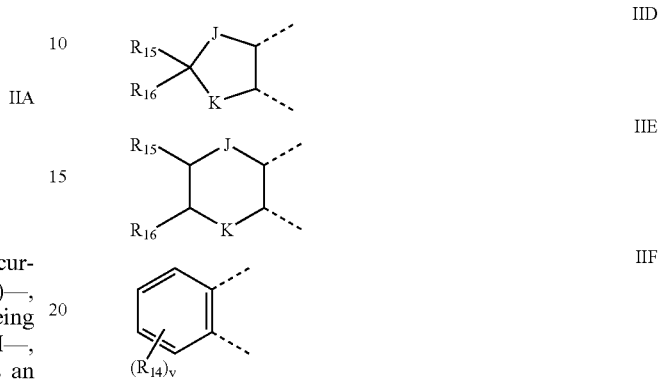

wherein J and K being independently chosen for each occurrence in each formula from oxygen or —NR$_{11}$—, R$_{11}$, R$_{14}$, R$_{15}$ and R$_{16}$ each being the same as described herein before, and n is an integer chosen from 0, 1, 2, 3 or 4.

In a further non-limiting embodiment, R$_2$ is the same as described herein before in (iv).

In another non-limiting embodiment, B and B' are each independently chosen from:

(i) mono-T-substituted phenyl wherein the group T is represented by the formula:

-Z[(OC$_2$H$_4$)$_x$(OC$_3$H$_6$)$_y$(OC$_4$H$_8$)$_z$]Z' or

-[(OC$_2$H$_4$)$_x$(OC$_3$H$_6$)$_y$(OC$_4$H$_8$)$_z$]Z' wherein -Z is —C(O)— or —CH$_2$—, Z' is C$_1$–C$_{12}$ alkoxy or a polymerizable group, x, y and z are each an number between 0 and 50, and the sum of x, y and z is between 2 and 50;

(ii) an unsubstituted, mono-, di-, or tri-substituted aryl group;

(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, each of said aryl and heteroaromatic substituents in (ii) and (iii) being independently chosen from hydroxy, the group, —C(O)W, defined hereinbefore, aryl, mono(C$_1$–C$_{12}$)alkoxyaryl, di(C$_1$–C$_{12}$)alkoxyaryl, mono(C$_1$–C$_{12}$)alkylaryl, di(C$_1$–C$_{12}$)alkylaryl, haloaryl, C$_3$–C$_7$ cycloalkylaryl, C$_3$–C$_7$ cycloalkyl, C$_3$–C$_7$ cycloalkyloxy, C$_3$–C$_7$ cycloalkyloxy(C$_1$–C$_{12}$)alkyl, C$_3$–C$_7$ cycloalkyloxy(C$_1$–C$_{12}$)alkoxy, aryl(C$_1$–C$_{12}$)alkyl, aryl(C$_1$–C$_{12}$)alkoxy, aryloxy, aryloxy(C$_1$–C$_{12}$)alkyl, aryloxy(C$_1$–C$_{12}$)alkoxy, mono- or di-(C$_1$–C$_{12}$)alkylaryl(C$_1$–C$_{12}$)alkyl, mono- or di-(C$_1$–C$_{12}$)alkoxyaryl(C$_1$–C$_{12}$)alkyl, mono- or di-(C$_1$–C$_{12}$)alkylaryl(C$_1$–C$_{12}$)alkoxy, mono- or di-(C$_1$–C$_{12}$)alkoxyaryl(C$_1$–C$_{12}$)alkoxy, amino, mono (C$_1$–C$_{12}$)alkylamino, di(C$_1$–C$_{12}$)alkylamino, diarylamino, piperazino, N-($C_1$–$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_{12}$ alkyl, $C_1$–$C_{12}$ haloalkyl, $C_1$–$C_{12}$ alkoxy, mono($C_1$–$C_{12}$)alkoxy ($C_1$–$C_{12}$)alkyl, acryloxy, methacryloxy, or halogen;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$–$C_{12}$ alkyl, $C_1$–$C_{12}$ alkoxy, phenyl or halogen;

(v) a monosubstituted phenyl, said phenyl having a substituent located at the para position being —$(CH_2)_t$— or —O—$(CH_2)_t$—, wherein t is chosen from the integer 1, 2, 3, 4, 5 or 6, said substituent being connected to an aryl group on another photochromic material;

(vi) a group represented by one of the following graphic formulae IIG or IIH:

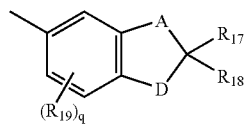

IIG

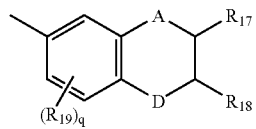

IIH wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$–$C_{12}$ alkyl, or $C_2$–$C_{12}$ acyl; each $R_{19}$ being independently chosen for each occurrence in each formula from $C_1$–$C_{12}$ alkyl, $C_1$–$C_{12}$ alkoxy, hydroxy, or halogen; $R_{17}$ and $R_{18}$ each being independently chosen in each formula from hydrogen or $C_1$–$C_{12}$ alkyl; and q being chosen from the integer 0, 1 or 2;

(vii) $C_1$–$C_{12}$ alkyl, $C_1$–$C_{12}$ haloalkyl, $C_1$–$C_{12}$ alkoxy ($C_1$–$C_{12}$)alkyl, $C_3$–$C_7$ cycloalkyl, mono($C_1$–$C_{12}$) alkoxy ($C_3$–$C_7$)cycloalkyl, mono($C_1$–$C_{12}$)alkyl ($C_3$–$C_7$)-cycloalkyl, halo($C_3$–$C_7$)cycloalkyl, or $C_4$–$C_{12}$ bicycloalkyl, provided that both B and B' are not chosen from (vii);

(viii) a group represented by the following graphic formula IIJ:

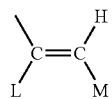

IIJ wherein L being chosen from hydrogen or $C_1$–$C_{12}$ alkyl and M being chosen from an unsubstituted, mono-, or di-substituted group chosen from naphthyl, phenyl, furanyl, or thienyl; each of said group substituents being independently chosen from $C_1$–$C_{12}$ alkyl, $C_1$–$C_{12}$ alkoxy, or halogen.

Alternatively, B and B' taken together form a fluoren-9-ylidene, mono-, or di- substituted fluoren-9-ylidene or a spirocyclic group chosen from saturated $C_3$–$C_{12}$ spiro-monocyclic hydrocarbon rings, saturated $C_7$–$C_{12}$ spiro-bi-cyclic hydrocarbon rings, or saturated $C_7$–$C_{12}$ spiro-tricyclic hydrocarbon rings, provided that said spirocyclic group is not norbornylidene or bicyclo[3.3.1]9-nonylidene each of said fluoren-9-ylidene substituents being independently chosen from $C_1$–$C_{12}$ alkyl, $C_1$–$C_{12}$ alkoxy or halogen.

Non-limiting examples of $C_3$–$C_{12}$ spiro-monocyclic hydrocarbon rings include cyclopropylidene, cyclobutylidene, cyclopentylidene, cyclohexylidene, cycloheptylidene, cyclooctylidene, cyclononylidene, cyclodecylidene cycloundecylidene or cyclododecylidene. Non-limiting examples of saturated $C_7$–$C_{12}$ spiro-bicyclic hydrocarbon rings include 1,7,7-trimethyl bicyclo[2.2.1]heptylidene, i.e., bornylidene, bicyclo[3.2.1]octylidene or bicyclo[4.3.2]undecane. Non-limitng examples of saturated $C_7$–$C_{12}$ spiro-tricyclic hydrocarbon rings include tricyclo[2.2.1.0$^{2,6}$]heptylidene, tricyclo[3.3.1.1$^{3,7}$]decylidene, i.e., adamantylidene, and tricyclo[5.3.1.1$^{2,6}$]dodecylidene.

In another non-limiting embodiment, the composition of the present invention comprises at least one material represented by at least one of the graphic formulae or mixtures thereof:

(a) $R_{11}$ is chosen from hydrogen, $C_1$–$C_{12}$ alkyl, $C_1$–$C_{12}$ acyl, phenyl($C_1$–$C_{12}$)alkyl, $C_1$–$C_{12}$ alkoxy($C_1$–$C_{12}$)alkyl or —CH($R_3$)Q, wherein $R_3$ being chosen from hydrogen or $C_1$–$C_{12}$ alkyl and Q is —COOR$_4$ and $R_4$ is $C_1$–$C_{12}$ alkyl;

(b) $R_1$ is independently chosen for each occurrence from:

(i) hydrogen, hydroxy, $C_1$–$C_{12}$ alkyl, vinyl, $C_3$–$C_7$ cycloalkyl, $C_1$–$C_{12}$ haloalkyl, allyl, benzyl or mono-substituted benzyl; each of said benzyl substituents being $C_1$–$C_{12}$ alkyl or $C_1$–$C_{12}$ alkoxy;

(ii) phenyl or mono-substituted phenyl; each of said phenyl substituents in (ii) being chosen independently for each occurrence from chloro, fluoro, $C_1$–$C_{12}$ alkyl or $C_1$–$C_{12}$ alkoxy;

(iii) a mono-substituted phenyl, said phenyl having a substituent located at the para position being —O—$(CH_2)_t$—, wherein t is chosen from the integer 1, 2, 3 or 4, said substituent being connected to an aryl group on another photochromic material;

(iv) —OR$_2$, $R_2$ being chosen from $R_{11}$;

(v) —CH(Q')$_2$, Q' is —COOR$_6$ and $R_6$ is $C_1$–$C_{12}$ alkyl;

(vi) —CH($R_7$)G, $R_7$ is hydrogen or $C_1$–$C_{12}$ alkyl, and G is —COOR$_5$ or —CH$_2$OR$_9$, wherein $R_8$ is $C_1$–$C_{12}$ alkyl and $R_9$ is $C_1$–$C_{12}$ alkyl or $C_1$–$C_{12}$ alkoxy($C_1$–$C_{12}$)alkyl;

(vii) the group T represented by the formula:

$$-Z[(OC_2H_4)_x(OC_3H_6)_y(OC_4H_8)_z]Z' \text{ or}$$

$$-[(OC_2H_4)_x(OC_3H_6)_y(OC_4H_8)_z]Z'$$

wherein -Z is —CH$_2$—, Z' is $C_1$–$C_{12}$ alkoxy or a polymerizable group, x, y and z are each an number between 0 and 20, and the sum of x, y and z is between 2 and 20;

(viii) —SR$_{10}$, R$_{10}$ is C$_1$–C$_{12}$ alkyl;
(ix) —N(R$_{11}$)R$_{12}$, R$_{12}$ is the same as R$_{11}$ described herein before;
(x) a nitrogen containing ring represented by the following graphic formula IIA:

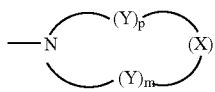

IIA wherein each Y being independently chosen for each occurrence from —CH$_2$— or —CH(R$_{13}$)—; X being —Y—, —O—, —S—, —NH—, —NR$_{13}$— or —N-aryl; R$_{13}$ being C$_1$–C$_{12}$ alkyl; m is the integer 1, 2 or 3 and p is an integer chosen from 0, 1, 2 or 3; provided that when p is 0, X is Y;

(xi) a group represented by one of the following graphic formulae IIB or IIC:

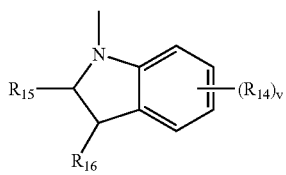

IIB

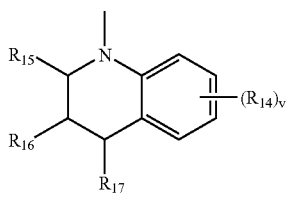

IIC wherein R$_{15}$, R$_{16}$ and R$_{17}$ are each independently chosen for each occurrence in each formula from hydrogen or C$_1$–C$_{12}$ alkyl, R$_{14}$ is independently chosen for each occurrence from C$_1$–C$_{12}$ alkyl, C$_1$–C$_{12}$ alkoxy, fluoro or chloro and v being chosen from the integer 0, 1 or 2; or (xii) adjacent R$_1$ substituents come together to form one of the following graphic formulae IID or IIF:

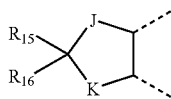

IID

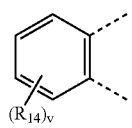

IIF wherein J and K being independently chosen for each occurrence in each formula from oxygen or —NR$_{11}$—, wherein R$_{11}$, R$_{14}$, R$_{15}$ and R$_{16}$ each being the same as described herein before;

(c) R$_2$ is chosen from R$_{11}$; and (d) B and B' are each chosen from:
(i) phenyl, mono- and di-substituted phenyl;
(ii) the unsubstituted, mono- and di-substituted heteroaromatic groups furanyl, benzofuran-2-yl, thienyl and benzothien-2-yl, each of said phenyl and heteroaromatic substituents in (i) and (ii) being chosen from C$_1$–C$_{12}$ alkyl, C$_1$–C$_{12}$ alkoxy and fluoro; or
(iii) the group represented by graphic formula IIG, wherein A is carbon and D is oxygen, R$_{19}$ is C$_1$–C$_{12}$ alkyl or C$_1$–C$_{12}$ alkoxy, R$_{17}$ and R$_{18}$ are each hydrogen or C$_1$–C$_{12}$ alkyl, and q is the integer 0 or 1.

Materials represented by graphic formulae I and I' described hereinbefore are prepared by methods known to those skilled in the art, for example, by the methods of the following Reactions A through G.

With references to the following Reactions A through G for producing the materials represented by graphic formula I and/or I' in one non-limiting illustration in Reaction A, the compounds represented by graphic formula III and IV are reacted in the presence of anhydrous ether and gaseous hydrochloric acid to form the ethoxycarbonylacetimidate represented by graphic formula V. See S. A. Glickman et al., *J. Am. Chem. Soc.* (1945), vol. 65, p. 1017. With reference to the following Reactions A and B, R is a substituent such as an alkyl or allyl, R$_1$ and R$_2$ are the same as described hereinbefore.

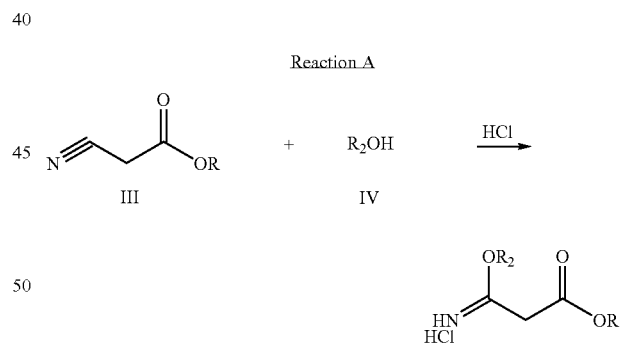

Reaction A

Further by way of non-limiting illustration in Reaction B, the ethoxycarbonylacetimidate acid complex represented by graphic formula V is reacted with an aniline represented by graphic formula VI in a suitable solvent such as ethanol to form the ethyl N-aryl-2-ethoxycarbonylacetimidate represented by graphic formula VII. The compound represented by graphic formula VII is heated in the presence of diphenyl ether and biphenyl in a ring-closing reaction to form the quinolone represented by graphic formula VIII. See N. D. Harris, *Synthesis* (1976), p. 826.

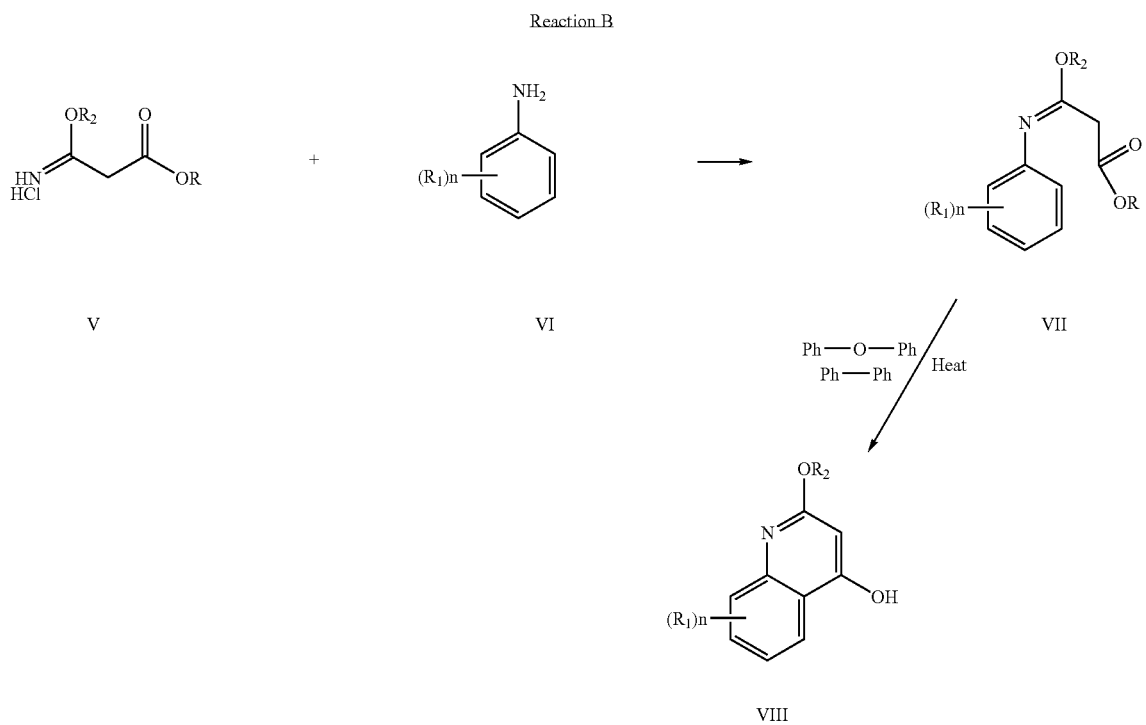

Compounds represented by graphic formula XI in Reaction C or XIA in Reaction D are either purchased or prepared by methods known to those skilled in the art, for example, by Friedel-Crafts methods shown in Reaction C using an appropriately substituted or unsubstituted benzoyl chloride of graphic formula IX with a commercially available substituted or unsubstituted benzene compound of graphic formula X. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

Further by way of non-limiting illustration in Reaction C the compounds represented by graphic formulae IX and X are dissolved in a solvent, such as carbon disulfide or methylene chloride, and reacted in the presence of a Lewis acid, such as aluminum chloride or tin tetrachloride, to form the corresponding substituted benzophenone represented by graphic formula XI (XIA in Reaction D and Reaction E). R' and R" represent possible substituents, as described hereinbefore with respect to B and B' of graphic formulae I and I'.

Reaction C

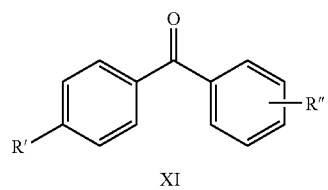

-continued

Further by way of non-limiting illustration in Reaction D, the substituted or unsubstituted ketone represented by graphic formula XIA, in which B and B' can represent groups other than substituted or unsubstituted phenyl, as shown in graphic formula XI, is reacted with sodium acetylide in a suitable solvent, such as anhydrous tetrahydrofuran (THF), to form the corresponding propargyl alcohol represented by graphic formula XII. Propargyl alcohols having B or B' groups other than substituted and unsubstituted phenyl can, for example, be prepared from commercially available ketones or ketones prepared via reaction of an acyl halide with a substituted or unsubstituted benzene, naphthalene or heteroaromatic compound, e.g., 9-julolidinyl. Propargyl alcohols having a B or B' group represented by graphic formula IIJ can, for example, be prepared by the methods described in U.S. Pat. No. 5,274,132, column 2, lines 40 to 68. The compound represented by graphic formula XII is dissolved in a suitable solvent such as ethanol and an acid such as hydrochloric acid is added dropwise to form the aldehyde of graphic formula XIII.

Reaction D

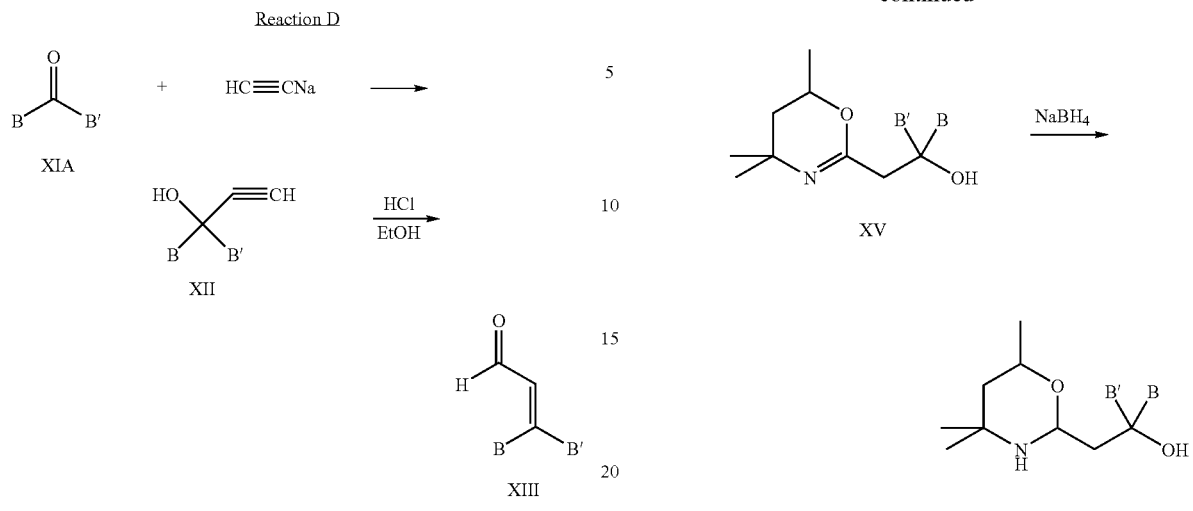

Another non-limiting illustration of a route for producing the aldehyde represented in graphic formula XIII is set forth in Reaction E. In the non-limiting illustration in Reaction E, an oxazine represented by graphic formula XIV is dissolved in a suitable solvent such as tetrahydrofuran (THF) to which n-butyl lithium is added. The ketone represented by graphic formula XIA dissolved in a suitable solvent such as THF is added to the oxazine mixture to produce the dihydrooxazine represented by graphic formula XV. Hydrogenation of the dihydrooxazine of graphic formula XV via addition of sodium borohydride yields the tetrahydrooxazine represented by graphic formula XVI. Upon heating of the tetrahydrooxazine of graphic formula XVI and adding of acid such as oxalic acid, the aldehyde of graphic formula XIII forms. See A. I. Meyers et al., *J. Org. Chem.* (1973), vol. 38 p. 36.

Reaction E

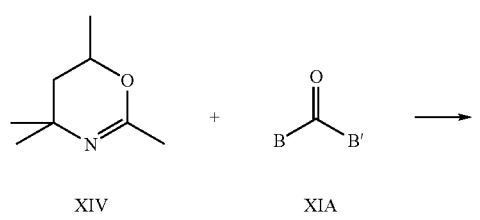

Further by way of non-limiting illustration in Reaction F, the aldehyde represented by graphic formula XIII e is dissolved in a suitable solvent such as toluene containing piperidine. Upon addition of acetic anhydride, an imminium solution is produced. The quinolone represented by graphic formula VIII is added to the imminium solution to react with the components thereof and form the quinolinopyran represented by graphic formula I'A.

Reaction F

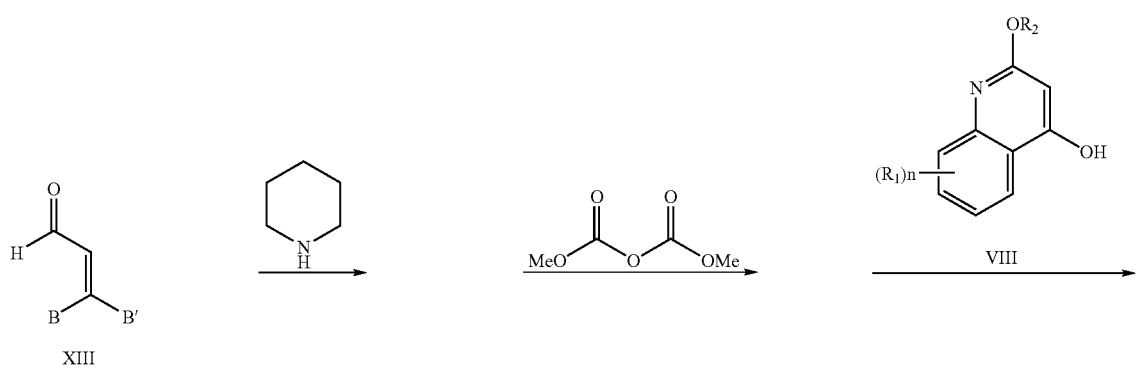

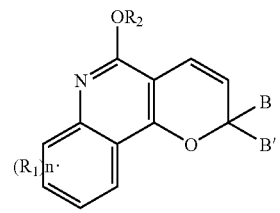

Further by way of non-limiting illustration in Reaction G, the aldehyde represented by graphic formula XIII is dissolved in a suitable solvent such as toluene containing piperidine. Upon addition of acetic anhydride, an imminium solution is produced. The quinolone represented by graphic formula VIIIA is added to the imminium solution to react with the components thereof and form the isomeric pyrano[3,2-c]quinoline and pyrano[3,2-c]quinolinone materials represented by graphic formulae I'B and IA, respectively.

The hydroxy substituent of the material represented by graphic formula I'B can be converted to an alkoxy substituent by reaction with an alkyl halide, e.g., methyl iodide, ethyl iodide, benzyl bromide, to produce the material represented by graphic formula I'C. The hydrogen substituent of the nitrogen atom of the material represented by graphic formula IA can be replaced by the substituent $R_{11}$ to yield the material represented by graphic formula IB.

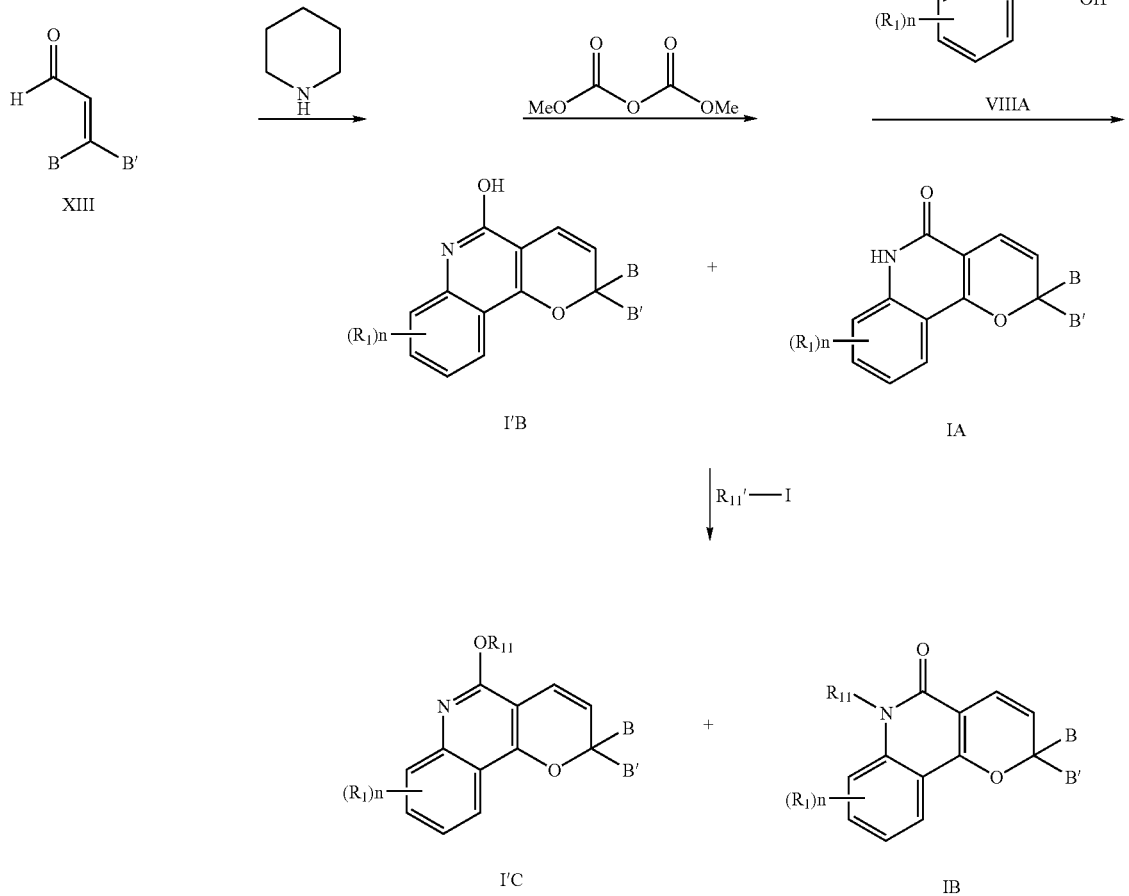

In another non-limiting embodiment, the composition of the present invention comprises an isomeric mixture of materials represented by graphic formulae I'B and IA wherein the isomeric mixture comprises:
(a) 2,2-diphenyl-2H-pyrano[3,2-c]quinolin-5-ol; and
(b) 2,2-diphenyl-5,6-dihydro-2H-pyrano[3,2-c]quinolin-5-one.

Non-limiting examples of compounds within the scope of the invention include at least one compound chosen from:
(a) 5-methoxy-2,2-diphenyl-2H-pyrano[3,2-c]quinoline;
(b) 5-ethoxy-2,2-diphenyl-2H-pyrano[3,2-c]quinoline;
(c) 5-ethoxy-9-methoxy-2,2-diphenyl-2H-pyrano[3,2-c]quinoline;
(d) 5-ethoxy-7-methoxy-2,2-diphenyl-2H-pyrano[3,2-c]quinoline;
(e) 12-ethoxy-3,3-diphenyl-3H-benzo[h]pyrano[3,2-c]quinoline;
(f) 5-ethoxy-7,9-dimethoxy-2,2-diphenyl-2H-pyrano[3,2-c]quinoline;
(g) 5-ethoxy-9-fluoro-2,2-diphenyl-2H-pyrano[3,2-c]quinoline;
(h) 2-(2,4-dimethoxyphenyl)-5-ethoxy-9-methoxy-2-(4-methoxyphenyl)-2 H-pyrano[3,2-c]quinoline;
(i) 12-ethoxy-3-(2-fluorophenyl)-3-(4-methoxy)-3H-benzo[h]pyrano[3,2-c]quinoline;
(j) 5-ethoxy-2-(2-fluorophenyl)-9-methoxy-2-(4-methoxyphenyl)-2H-pyrano[3,2-c]quinoline;
(k) 5-ethoxy-2-(2-fluorophenyl)-7-methoxy-2-(4-methoxyphenyl)-2H-pyrano[3,2-c]quinoline;
(l) 5-ethoxy-3-(2-fluorophenyl)-3-(4-methoxy)-2H-[1,3]-dioxolo[4,5-g]pyrano[3,2-c]quinoline;
(m) 12-ethoxy-3-(2,4-dimethoxyphenyl)-3-(4-methoxyphenyl)-3H-benzo[h]pyrano[3,2-c]quinoline;
(n) 2,2-diphenyl-6-methyl-5,6-dihydro-2H-pyrano[3,2-c]quinolin-5-one: or
(o) mixtures thereof.

Each of the pyrano[3,2-c]quinolines and/or pyrano[3,2-c]quinolinones can be used with or without the other photochromic materials described herein in amounts (or in ratios) that can vary widely. Generally, an amount is used so that a host material or substrate with which the photochromic material is associated, exhibits a desired resultant color, e.g., a substantially neutral color when activated with unfiltered sunlight. The photochromic materials, could be used to produce articles having a wide range of colors, e.g., pink, blue, orange, etc. Further discussion of neutral colors and ways to describe colors can be found in U.S. Pat. No. 5,645,767 column 12, line 66 to column 13, line 19.

In one non-limiting embodiment, it is contemplated that photochromic material of the present invention can be used alone or in combination with other such materials of the present invention, or in combination with one or more other photochromic materials, e.g., photochromic materials having at least one activated absorption maxima within the range of between about 400 and 700 nanometers.

In another non-limiting embodiment, the other photochromic materials can include the following classes of materials: chromenes, e.g., naphthopyrans, benzopyrans, indenonaphthopyrans, phenanthropyrans or mixtures thereof; spiropyrans, e.g., spiro(benzindoline)naphthopyrans, spiro(indoline)benzopyrans, spiro(indoline)naphthopyrans, spiro(indoline)quinopyrans and spiro(indoline)pyrans; oxazines, e.g., spiro(indoline)naphthoxazines, spiro(indoline)pyridobenzoxazines, spiro(benzindoline)pyridobenzoxazines, spiro(benzindoline)naphthoxazines and spiro(indoline)benzoxazines; mercury dithizonates, fulgides, fulgimides and mixtures of such photochromic materials.

Such photochromic materials and complementary photochromic materials are described in U.S. Pat. No. 4,931,220 at column 8, line 52 to column 22, line 40; U.S. Pat. No. 5,645,767 at column 1, line 10 to column 12, line 57; U.S. Pat. No. 5,658,501 at column 1, line 64 to column 13, line 17; U.S. Pat. No. 6,153,126 at column 2, line 18 to column 8, line 60; U.S. Pat. No. 6,296,785 at column 2, line 47 to column 31, line 5; U.S. Pat. No. 6,348,604 at column 3, line 26 to column 17, line 15; and U.S. Pat. No. 6,353,102 at column 1, line 62 to column 11, line 64, the disclosures of the aforementioned patents are incorporated herein by reference. Spiro(indoline)pyrans are also described in the text, *Techniques in Chemistry*, Volume III, "Photochromism", Chapter 3, Glenn H. Brown, Editor, John Wiley and Sons, Inc., New York, 1971.

In a further non-limiting embodiment, the other photochromic materials can be polymerizable photochromic materials, such as polymerizable naphthoxazines disclosed in U.S. Pat. No. 5,166,345 at column 3, line 36 to column 14, line 3; polymerizable spirobenzopyrans disclosed in U.S. Pat. No. 5,236,958 at column 1, line 45 to column 6, line 65; polymerizable spirobenzopyrans and spirobenzothiopyrans disclosed in U.S. Pat. No. 5,252,742 at column 1, line 45 to column 6, line 65; polymerizable fulgides disclosed in U.S. Pat. No. 5,359,085 at column 5, line 25 to column 19, line 55; polymerizable naphthacenediones disclosed in U.S. Pat. No. 5,488,119 at column 1, line 29 to column 7, line 65; polymerizable spirooxazines disclosed in U.S. Pat. No. 5,821,287 at column 3, line 5 to column 11, line 39; polymerizable polyalkoxylated naphthopyrans disclosed in U.S. Pat. No. 6,113,814 at column 2, line 23 to column 23, line 29; and the polymerizable photochromic materials disclosed in WO97/05213 and allowed U.S. application Ser. No. 09/828,260 filed Apr. 6, 2001. The disclosures of the aforementioned patents on polymerizable photochromic materials are incorporated herein by reference.

Other non-limiting embodiments of photochromic materials that can be used include organo-metal dithiozonates, e.g., (arylazo)-thioformic arylhydrazidates, e.g., mercury dithizonates which are described in, for example, U.S. Pat. No. 3,361,706 at column 2, line 27 to column 8, line 43; and fulgides and fulgimides, e.g., the 3-furyl and 3-thienyl fulgides and fulgimides, which are described in U.S. Pat. No. 4,931,220 at column 1, line 39 through column 22, line 41, the disclosures of which are incorporated herein by reference.

An additional non-limiting embodiment of the other photochromic materials is a form of organic photochromic material substantially resistant to the effects of a polymerization initiator that can also be used in the photochromic articles of the present invention. Such organic photochromic materials include photochromic compounds in admixture with a resinous material that has been formed into particles and encapsulated in metal oxides, which are described in U.S. Pat. Nos. 4,166,043 and 4,367,170 at column 1 line 36 to column 7, line 12, which disclosure is incorporated herein by reference.

The photochromic materials described herein, e.g., the photochromic composition of the present invention and other photochromic materials, can be chosen from a variety of materials. Non-limiting examples include: of course, a single photochromic compound; a mixture of photochromic compounds; a material comprising at least one photochromic compound, such as a plastic polymeric resin or an organic monomeric or oligomeric solution; a material such as a monomer or polymer to which at least one photochromic compound is chemically bonded; a material comprising and/or having chemically bonded to it at least one photochromic compound, the outer surface of the material being encapsulated (encapsulation is a form of coating), for example with a polymeric resin or a protective coating such as a metal oxide that prevents contact of the photochromic material with external materials such as oxygen, moisture and/or chemicals that have a negative effect on the photochromic material, such materials can be formed into a particulate prior to applying the protective coating as described in U.S. Pat. Nos. 4,166,043 and 4,367,170; a photochromic polymer, e.g., a photochromic polymer comprising polymerized photochromic monomers; or mixtures thereof.

In one non-limiting embodiment, the amount of the photochromic materials to be incorporated into a polymeric coating composition and/or polymeric host material can vary widely. Generally a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate the photochromic materials. Typically, in one non-limiting embodiment, the more photochromic material incorporated, the greater is the color intensity up to a certain limit. There is a point after which the addition of any more material will not have a noticeable effect, although more material may be added, if desired.

The relative amounts of the aforesaid photochromic materials used will vary and depend in part upon the relative intensities of the color of the activated species of such materials, the ultimate color desired, and the method of application to the host material and/or substrate. In one non-limiting embodiment, the amount of total photochromic material which includes the photochromic material of the present invention, other photochromic materials or both, incorporated by imbibition into a photochromic optical host material can vary widely. For example, generally it can range from about 0.01 to about 2.0, e.g., from 0.05 to about 1.0, milligrams per square centimeter of surface to which the photochromic material is incorporated or applied. The amount of total photochromic material incorporated or applied to the host material can range between any combination of these values, inclusive of the recited range, e.g., 0.015 to 1.999 milligrams per square centimeter.

In another non-limiting embodiment, the total amount of photochromic material incorporated into a polymerizable composition for forming a coating or polymerizate can vary widely. For example, it can range from 0.01 to 40 weight percent based on the weight of the solids in the polymerizable composition. In alternate non-limiting embodiments, the concentration of photochromic materials generally can range from 0.1 to 30 weight percent, from 1 to 20 weight percent, from 5 to 15 weight percent, or from 7 to 14 weight percent. The amount of photochromic material in the coating can range between any combination of these values, inclusive of the recited range, e.g., 0.011 to 39.99 weight percent.

In one non-limiting embodiment, compatible (chemically and color-wise) fixed tint dyes, can be added or applied to the host material, e.g., polymeric substrate, polymeric coating and/or polymeric film, used to produce the photochromic article to achieve a more aesthetic result, for medical reasons, or for reasons of fashion. The particular dye selected will vary and depend on the aforesaid need and result to be achieved. In one non-limiting embodiment, the dye can be selected to complement the color resulting from the activated photochromic materials, e.g., to achieve a more neutral color or absorb a particular wavelength of incident light. In another non-limiting embodiment, the dye can be selected to provide a desired hue to the host material when the photochromic materials are in an unactivated state.

In various non-limiting embodiments, adjuvant materials can also be incorporated into the host material used to produce the photochromic article. Such adjuvants can be used, prior to, simultaneously with or subsequent to application or incorporation of the photochromic material. For example, ultraviolet light absorbers can be admixed with photochromic materials before their addition to the composition or such absorbers can be superposed, e.g., superimposed, as a coating between the photochromic article and the incident light.

Further, stabilizers can be admixed with the photochromic materials prior to their addition to the composition to improve the light fatigue resistance of the photochromic materials provided that such stabilizers do not prevent the photochromic materials from activating. Non-limiting examples of stabilizers include hindered amine light stabilizers (HALS), asymmetric diaryloxalamide (oxanilide) compounds and singlet oxygen quenchers, e.g., a nickel ion complex with an organic ligand, polyphenolic antioxidants or mixtures of such stabilizers are contemplated. In one non-limiting embodiment, they can be used alone or in combination. Such stabilizers are described in U.S. Pat. Nos. 4,720,356, 5,391,327 and 5,770,115.

The composition of the present invention, other photochromic materials or combinations thereof can be associated with the host material by various methods described in the art. In various non-limiting embodiments, the total amount of photochromic material can be incorporated into the host material used to form the photochromic article by various methods such as by adding the photochromic materials to one or more of the materials used to form the host material. In one non-limiting embodiment when the host material is a polymeric coating or film, the photochromic materials can be dissolved and/or dispersed in an aqueous or organic solvent prior to being incorporated into one or more of the components of the composition used to form the coating or film. Alternatively, the photochromic materials can be incorporated into the at least partially cured coating by imbibition, permeation or other transfer methods as known by those skilled in the art.

When at least partially cured polymers or polymerizates are used as the host material for the photochromic materials, various non-limiting embodiments include preparation of a photochromic article by injecting a polymerizable composition with photochromic materials with or without polymerizable substituents into a mold and polymerizing it by what, for example, is commonly referred to in the art as a cast-in-place process. In another non-limiting embodiment, photochromic materials can be added with the materials used to produce a polymeric film by extrusion or other methods known to those skilled in the art. Polymerizates, e.g., lenses, prepared by cast polymerization in the absence of a photochromic amount of a photochromic material can be used to prepare photochromic articles by applying or incorporating photochromic materials into the polymerizate by art-recognized methods.

Such non-limiting art-recognized methods include: (a) dissolving, dispersing and/or reacting the photochromic materials with or without polymerizable substituents with the materials used to form the polymerizate, e.g., addition of photochromic materials to a polymerizable composition or imbibition of the photochromic materials into the polymerizate by immersion of the polymerizate in a hot solution of the photochromic materials or by thermal transfer; (b) providing the photochromic material as a separate coating between adjacent coatings of the polymerizate, e.g., as a part of a polymer film; and (c) applying the photochromic material as part of a coating or film placed or laminated on the surface of the polymerizate. The term "imbibition" or "imbibe" is intended to mean and include permeation of the photochromic materials individually or with other non-photochromic materials into the polymerizate, solvent assisted transfer absorption of the photochromic materials into a polymerizate, vapor phase transfer, and other such transfer mechanisms.

In the context of the present invention, the nature of the polymeric organic material used as the host, substrate, film or coating can vary widely. Generally the polymeric organic material is such that it allows the photochromic materials of the present invention and other photochromic materials to reversibly transform between their "open" and "closed" forms. In one non-limiting embodiment, the polymeric organic material used to produce the photochromic articles of the present invention comprises compositions adapted to provide thermoplastic or thermosetting organic polymeric materials that are described in the *Kirk-Othmer Encyclopedia of Chemical Technology*, Fourth Edition, Volume 6, pages 669 to 760, which disclosure is incorporated herein by reference. Such polymeric materials can be transparent, translucent or opaque; but desirably are transparent or optically clear. In another non-limiting embodiment, the film forming polymer used in the coating is one that upon curing forms an at least partially cured polymeric coating that is thermosetting and chosen from polyurethanes, aminoplast resins, poly(meth)acrylates, e.g., polyacrylates and polymethacrylates, polyanhydrides, polyacrylamides, epoxy resins and polysilanes. The phrase "an at least partially cured polymeric coating" refers to a coating in which the curable or cross-linkable components are at least partially cured, crosslinked and/or reacted in the same manner as described hereinbefore for "an at least partially cured polymeric host".

The various coating compositions described below are well known and are made with components and according to methods well understood and appreciated to those skilled in the art. Suitable substrates for the application of coatings containing the composition of the present invention or a mixture of the composition and other photochromic materials include any type of substrate. Non-limiting examples include, paper, glass, ceramics, wood, masonry, textiles, metals and polymeric organic host materials.

The photochromic polyurethane coatings that can be used to prepare the photochromic coated articles of the present invention, in one non-limiting embodiment, can be produced by combining a photochromic material with the catalyzed or uncatalyzed reaction of an organic polyol component and an isocyanate component. Materials and methods for the preparation of polyurethanes are described in *Ullmann's Encyclopedia of Industrial Chemistry*, Fifth Edition, 1992, Vol. A21, pages 665 to 716. Non-limiting examples of methods and materials, e.g., organic polyols, isocyanates and other components, which can be used to prepare the polyurethane coating are disclosed in U.S. Pat. Nos. 4,889,413 and 6,187,444B1.

The photochromic aminoplast resin coating composition that can be used to produce the photochromic coated articles of the present invention, in one non-limiting embodiment, can be prepared by combining a photochromic material with the reaction product of a functional component(s) having at least two functional groups chosen from hydroxyl, carbamate, urea or a mixture thereof and an aminoplast resin, e.g., crosslinking agent as described in U.S. Pat. Nos. 4,756,973, 6,432,544B1 and 6,506,488.

Photochromic polysilane coating compositions contemplated for use in preparing the photochromic coated articles of the present invention, in one non-limiting embodiment, are prepared by hydrolyzing at least one silane monomer such as glycidoxypropyltrimethoxysilane, vinyltrimethoxysilane, methacryloxypropyltrimethoxysilane, tetramethoxysilane, tetraethoxysilane and/or methyltrimethoxysilane and combining the hydrolyzate with at least one photochromic material as described in U.S. Pat. No. 4,556,605.

Photochromic poly(meth)acrylate coating compositions contemplated for use in preparing the photochromic coated articles of the present invention can be prepared, in one non-limiting embodiment, by combining photochromic materials with mono-, di- or multi-functional (meth)acrylates as described in U.S. Pat. Nos. 6,025,026 and 6,150,430 and WO publication 01/02449 A2.

The polyanhydride photochromic coating composition that can be used to prepare the photochromic coated articles of the present invention can be prepared in one non-limiting embodiment, by the reaction of a hydroxyl-functional component and a polymeric anhydride-functional component in a composition including at least one organic photochromic material as described in U.S. Pat. No. 6,432,544B1. Non-limiting examples of hydroxyl-functional components, anhydride-functional component(s) and other components that can be used to prepare the polyanhydride photochromic coatings are disclosed in U.S. Pat. Nos. 4,798,745, 4,798,746 and 5,239,012.

Photochromic polyacrylamide coating compositions contemplated for use in preparing the photochromic coated articles of the present invention, in one non-limiting embodiment, can be prepared by-combining a photochromic material with the free radical initiated reaction product of a polymerizable ethylenically unsaturated composition comprising N-alkoxymethyl(meth)acrylamide and at least one other copolymerizable ethylenically unsaturated monomer as described in U.S. Pat. No. 6,060,001. Methods for preparing N-alkoxymethyl(meth)acrylamide functional polymer are described in U.S. Pat. No. 5,618,586.

The photochromic epoxy resin coating compositions that can be used to prepare the photochromic coated articles of the present invention, in one non-limiting embodiment, can be prepared by combining photochromic materials, epoxy resins, or polyepoxides and curing agents as described in U.S. Pat. Nos. 4,756,973 and 6,268,055B1.

In another non-limiting embodiment, the types of photochromic polymeric coatings comprising the film-forming polymers and the composition of the present invention with or without other photochromic materials include paints, e.g., a pigmented liquid or paste used for the decoration, protection and/or the identification of a substrate; and inks, e.g., a pigmented liquid or paste used for writing and printing on substrates such as in producing verification marks on security documents, e.g., documents such as banknotes, passport and drivers' licenses, for which authentication or verification of authenticity may be desired.

Application of the polymeric coating can be by any of the methods used in coating technology, non-limiting examples include, spray coating, spin coating, spin and spray coating, spread coating, curtain coating, dip coating, casting or roll-coating and methods used in preparing overlays, such as the method of the type described in U.S. Pat. No. 4,873,029. The application method selected also depends on the thickness of the desired coating.

The thickness of the coatings on the photochromic articles of the present invention can vary widely. In alternate non-limiting embodiments, the coating may range in thickness from 1 to 10,000 microns, from 5 to 1000, from 8 to 400, or from 10 to 250 microns. The thickness of the polymeric coating can range between any combination of these values, inclusive of the recited range, e.g., a thickness of from 20 to 200 microns. Coating having a thickness ranging from 1 to 50 microns can be applied by the methods used in coating technology. Coating of a thickness greater than 50 microns can require the application of multiple coatings or molding methods typically used for overlays.

Following application of the polymeric coating to the surface of the substrate, in one non-limiting embodiment, the coating is at least partially cured. In another non-limiting embodiment, the methods used for curing the photochromic polymeric coating include the methods used for forming an at least partially cured polymer. Such methods include radical polymerization, thermal polymerization, photopolymerization or a combination thereof. Additional non-limiting methods include irradiating the coated substrate or at least partially cured polymer with infrared, ultraviolet, gamma or electron radiation-so as to initiate the polymerization reaction of the polymerizable components with or without a catalyst or initiator. This can be followed by a heating step.

In one non-limiting embodiment, if required and if appropriate, the surface of the substrate to be coated is cleaned prior to applying the photochromic polymeric coating to produce the photochromic article of the present invention. This can be done for the purposes of cleaning and/or promoting adhesion of the coating. Effective treatment techniques for plastics and glass are known to those skilled in the art.

In some non-limiting embodiments, it can be helpful to apply a primer to the surface of the substrate before application of the photochromic polymeric coating. The primer can serve as a barrier coating to prevent interaction of the coating ingredients with the substrate and vice versa, and/or as an adhesive layer to adhere the photochromic polymeric coating to the substrate. Application of the primer can be by any of the methods used in coating technology such as, for example, spray coating, spin coating, spin and spray coating, spread coating, dip coating, casting or roll-coating.

The use of protective coatings, some of which can contain polymer-forming organosilanes, as primers to improve adhesion of subsequently applied coatings has been described in U.S. Pat. No. 6,150,430, which disclosure is incorporated herein by reference. In one non-limiting embodiment, non-tintable coatings are used. Non-limiting examples of commercial coating products include SIL-VUE® 124 and HI-GARD® coatings, available from SDC Coatings, Inc. and PPG Industries, Inc., respectively. In-addition, depending on the intended use of the coated article, in one non-limiting embodiment, it can be necessary to apply an appropriate protective coating(s), such as an abrasion resistant coating and/or coatings that can serve as oxygen barriers, onto the exposed surface of the coating composition to prevent scratches from the effects of friction and abrasion and interactions of oxygen with the photochromic materials, respectively.

In some cases, the primer and protective coatings, for example hardcoats, are interchangeable, e.g., the same coating can be used as the primer and the protective coating(s).

Non-limiting examples of hardcoats include those based on inorganic materials such as silica, titania and/or zirconia as well as organic hardcoats of the type that are ultraviolet light curable. In one non-limiting embodiment, such protective coatings can be applied to the surface of photochromic articles comprising at least partially cured polymers containing photochromic materials.

In another non-limiting embodiment, the article of the present invention comprises a substrate to which a primer is applied followed by the photochromic polymeric coating and a protective hardcoat. In a further non-limiting embodiment, the protective hardcoat is a polysilane, e.g., an organosilane hardcoat.

In additional non-limiting embodiments, other coatings or surface treatments, e.g., a tintable coating, at least a partially antireflective coating, etc., can also be, applied to the photochromic articles of the present invention. An antireflective coating, e.g., a monolayer or multilayer of metal oxides, metal fluorides, or other such materials, can be deposited onto the photochromic articles, e.g., lenses, of the present invention through vacuum evaporation, sputtering, or some other method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the untreated surface. Put another way, the percent transmittance of the treated surface can range from a percentage greater than the untreated surface up to 99.9.

In a further non-limiting embodiment, the photochromic article comprising an at least partially cured polymer and a photochromic amount of at least one composition of the present invention with or without other photochromic material further comprises a superstrate, e.g., a film or sheet comprising at least one organic polymeric material. The photochromic material can be located in the superstrate, the at least partially cured polymer or both. The organic polymeric material of the superstrate is the same as the organic polymeric material described hereinafter as the substrate or host material. Non-limiting examples of the organic polymeric materials include thermosetting or thermoplastic materials, for example a thermoplastic polyurethane superstrate.

In a still further non-limiting embodiment, the superstrate can be connected to the polymer surface directly. As used herein and the claims, the term "connected to" means to link together or place in relationship either directly, or indirectly by one or more intervening materials. In another non-limiting embodiment, the superstrate can be connected, e.g., adherringly bonded, to the substrate by becoming thermally fused with the subsurface of the substrate. General conditions under which superstrates are adherringly bonded to a substrate are known to those skilled in the art. Non-limiting conditions for adherringly laminating a superstrate to a substrate include heating to a temperature of from 250–350° F. (121–177° C.) and applying pressure of from 150 to 400 pounds per square inch (psi)(1034 to 2758 kPa). Sub-atmospheric pressures, e.g., a vacuum, can also be applied to draw down and conform the superstrate to the shape of the substrate as known to those skilled in the art. Non-limiting examples include applying at a sub-atmospheric pressure within the range of from 0.001 mm Hg to 20 mm Hg (0.13 Pa to 2.7 kPa).

After a laminate comprising a superstrate applied to as least one surface of a substrate is formed, it can further comprise a protective coating or film superposed onto the superstrate. Such a protective coating or film, in one non-limiting embodiment, serves as an at least partially abrasion resistant coating or film. The phrase "an at least partially abrasion resistant coating or film" refers to a coating or film that demonstrates a Bayer Abrasion Resistance Index of from at least 1.3 to 10.0 in ASTM F-735 Standard Test Method for Abrasion Resistance of Transparent Plastics and Coatings Using the Oscillating Sand Method.

Non-limiting types of protective coatings include the aforedescribed hardcoats that are curable by ultraviolet radiation and/or that contain organosilanes. The thickness of the protective coating can vary widely and include the aforementioned range for the photochromic polymeric coatings. Non-limiting types of protective films include those made of organic polymeric materials such as thermosetting and thermoplastic materials. In another non-limiting embodiment, the protective film is a thermoplastic film made of polycarbonate. The thickness of the protective film or sheet can vary widely. Typically, such films have a thickness of from 1 to 20 mils (0.025 to 0.5 mm).

The host material for the compositions of the present invention with or without other photochromic materials will usually be transparent, but may be translucent or even opaque. The host material need only be pervious to that portion of the electromagnetic spectrum, which activates the photochromic material, e.g., that wavelength of ultraviolet (UV) light that produces the open or colored form of the photochromic and that portion of the visible spectrum that includes the absorption maximum wavelength of the photochromic material in its UV activated form, e.g., the open form. In one contemplated non-limiting embodiment, the host color should not be such that it masks the color of the activated form of the photochromic materials, e.g., so the change in color is readily apparent to the observer. Compatible tints may be applied to the host material as described in U.S. Pat. No. 5,645,767 in column 13, line 59 to column 14, line 3.

In one contemplated non-limiting embodiment, the polymeric organic material used as a host or substrate can be a solid transparent or optically clear material, e.g., materials having a luminous transmittance of at least 70 percent and are suitable for optical applications, chosen from thermosetting or thermoplastic organic polymeric materials. Examples of optical elements chosen from plano and ophthalmic lenses, ocular devices such as ophthalmic devices that physically reside in or on the eye, e.g., contact lenses and intraocular lenses, windows, automotive transparencies, e.g., windshields, aircraft transparencies, plastic sheeting, polymeric films, etc. In another non-limiting embodiment, the substrate or host is an optical element that is a lens, e.g. an ophthalmic lens.

Non-limiting examples of polymeric organic materials which can be used as a host material for the compositions of the present invention with or without other photochromic materials or as a substrate for the photochromic polymeric coating include: poly(meth)acrylates, polyurethanes, polythiourethanes, poly(urea-urethanes), thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral, poly(vinyl acetate), cellulose acetate, cellulose propionate, cellulose butyrate, cellulose acetate butyrate, polystyrene or polymers, such as homopolymers and copolymers prepared by polymerizing monomers chosen from bis(allyl carbonate) monomers, styrene monomers, diisopropenyl benzene monomers, vinylbenzene monomers, e.g., those described in U.S. Pat. No. 5,475,074, diallylidene pentaerythritol monomers, polyol (allyl carbonate) monomers, e.g., diethylene glycol bis(allyl carbonate), vinyl acetate monomers, acrylonitrile monomers, mono- or polyfunctional, e.g., di- or multi-functional, (meth)acrylate monomers such as ($C_1$–$C_{12}$)alkyl (methiacrylates, e.g., methyl (meth)acrylate, ethyl (meth)acrylate, butyl (meth)acrylate etc., poly(oxyalkylene)(meth)acrylate, poly(alkoxylated phenol (meth)acrylates), diethylene glycol (meth)acrylates, ethoxylated bisphenol A (meth)acrylates, ethylene glycol (meth)acrylates, poly(ethylene glycol) (meth)acrylates, ethoxylated phenol (meth)acrylates, alkoxylated polyhydric alcohol (meth)acrylates, e.g., ethoxylated trimethylol propane triacrylate monomers, urethane (meth)acrylate monomers, such as those described in U.S. Pat. No. 5,373,033, or a mixture thereof. Further examples of polymeric organic host materials are disclosed in the U.S. Pat. No. 5,753,146, column 8, line 62 to column 10, line 34.

In another non-limiting embodiment, transparent copolymers and blends of transparent polymers are also suitable as polymeric materials. The material can be an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the-material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483.

A further non-limiting embodiment is use of the composition of the present invention and other photochromic materials with optical organic resin monomers used to produce optically clear coatings and polymerizates, e.g., materials suitable for optical applications, such as for example plano and ophthalmic lenses, e.g., high refractive index lenses, windows, and automotive transparencies. Examples of non-limiting embodiments include polymerizates of optical resins sold by PPG Industries, Inc. as TRIVEX monomers and under the CR- designation, e.g., CR-307, CR-407 and CR-607 and the resins used to prepare hard or soft contact lenses. Methods for producing both types of contact lenses are disclosed in U.S. Pat. No. No. 5,166,345, column 11, line 52, to column 12, line 52.

Further non-limiting embodiments of optical resins include the resins used to form soft contact lenses with high moisture content described in U.S. Pat. No. No. 5,965,630 and extended wear contact lenses described in U.S. Pat. No. 5,965,631.

The present invention is more particularly described in the following examples that are intended as illustration only, since numerous modifications and variations therein will be apparent to those skilled in the art.

EXAMPLE 1

Step 1

Benzophenone (50 grams(g)) was dissolved in a reaction flask containing 200 milliliters (mL) of anhydrous tetrahydrofuran (THF) saturated with acetylene and stirred at room temperature. An 18 weight percent suspension of sodium acetylide in xylene/mineral oil (0.3 mol of sodium acetylide) was added to the reaction flask and the mixture was stirred. After-stirring 16 hours at room temperature under a nitrogen atmosphere, the contents of the reaction flask mixture was added to a 5 weight percent aqueous hydrochloric acid and ice mixture. The resulting mixture was extracted with diethyl ether. The organic layer was separated, washed, and dried over anhydrous sodium sulfate. The solvents, diethylether and THF, were removed under vacuum to yield an oil product containing 1,1-diphenyl-2-propyn-1-ol, which was not purified further but used directly in the next step.

Step 2

The oil containing 1,1-diphenyl-2-propyn-1-ol (20 g) from Step 1 was dissolved in 100 mL ethanol in a reaction flask. A few drops of concentrated hydrochloric acid were added to the solution. The solution was heated at 60° C. for 24 hours and was poured into an ice/water mixture and extracted with ether. The solvent was evaporated under vacuum to yield a red-colored gum that was flash column separated on alumina with hexane/ethyl acetate in a 80:20 volume ratio, and recrystallized from dichloromethane/hexane in a 80:20 volume ratio to give 16.5 g of a product. NMR analysis showed the product to have a structure consistent with β-phenylcinnamaldehyde.

Step 3

The β-phenylcinnamaldehyde from Step 2 (2.6 g) was dissolved in 20 mL of toluene in a reaction flask at 0° C. Piperidine (0.82 g) was added to the reaction flask and stirred for 10 minutes. Acetic anhydride (0.91 mL) was added and the reaction mixture was stirred at 80° C. for 1 hour. 2,4-Quinolinediol (purchased from Aldrich) (2 g) was added to the reaction flask, and the reaction mixture was refluxed for 24 hours. Following evaporation of the solvent, the residue was purified via flash column separation. A nuclear magnetic resonance (NMR) spectrum showed the product to have a structure consistent with 2,2-diphenyl-2H-pyrano[3,2-c]quinolin-5-ol and 2,2-diphenyl-5,6-dihydro-2H-pyrano[3,2-c]quinolin-5-one, the keto-isomer in equilibrium.

EXAMPLE 2

Two grams of 2,2-diphenyl-2H-pyrano[3,2-c]quinolin-5-ol were prepared as described in Example 1 and added with anhydrous potassium carbonate (2 g), and methyliodide (2 g) to a reaction flask containing 40 mL of anhydrous acetone. The mixture was stirred and refluxed under an argon atmosphere. Afterwards, the acetone was removed under vacuum and 25 mL each of water and methylene chloride were added to the reaction mixture. The mixture was stirred for 30 minutes, and the organic layer was separated, washed, and dried. The remaining solvent, methylene chloride, was removed under vacuum. The resulting oily concentrate was crystallized from a 1:1 hexane:methylene chloride mixture. The solid obtained was suction filtered, washed with hexane and dried. A NMR spectrum showed the product to have a structure consistent with 5-methoxy-2,2-diphenyl-2H-pyrano[3,2-c]quinoline.

EXAMPLE 3

Part A

Step 1

Ethyl cyanoacetate (113 g), absolute ethyl alcohol (50 g) and dry ether (50 g) were added to a one-liter flask and cooled in an ice bath. Dry hydrochloric acid was passed thorough the solution until the increase in weight was 42 g. The flask was stoppered with a rubber septa and refrigerated for 24 hours. The reaction mixture was filtered and the residue was washed with hexane several times and dried under a vacuum to yield 150 g of a hydrochloride product. A nuclear magnetic resonance (NMR) spectrum showed the product to have a structure consistent with ethyl-β-amino-Z-ethoxyacrylate hydrochloride.

Part A

Step 2

The ethyl-β-amino-β-ethoxyacrylate hydrochloride produced in Step 1 (64.6 g) was added to a reaction flask containing a solution of aniline (30.7 g ) in 600 (mL) of ethanol. The mixture was stirred for 24 hours at room temperature and filtered. The recovered solid was washed with ethanol. The combined filtrates were evaporated and the residue was slurried in chloroform and filtered. Upon evaporation of the solvent, 45.6 g of a product was recovered via vacuum distillation. A NMR spectrum showed the product to have a structure consistent with ethyl-N-phenyl-2-ethoxycarbonylacetimidate.

Part A

Step 3

The ethyl-N-phenyl-2-ethoxycarbonylacetimidate of Step 2 was added to a reaction vessel containing 100 mL of Dowtherm A (a mixture of diphenyl ether and 26.5% biphenyl available from Dow Chemical Company) refluxing at 260° C. for 30 minutes. The resulting mixture was cooled and diluted with 500 mL hexane. The reaction mixture was filtered and the residue was washed several times with hexane and dried under vacuum yielding 6.4 g of a product. A NMR spectrum showed the product to have a structure consistent with 2-ethoxy-4-hydroxyquinoline.

Part B

The β-phenylcinnamaldehyde from Step 2 of Example 1, (2 g) was dissolved in 20 mL of toluene in a reaction flask at 0° C. Piperidine (0.82 g) was added to the reaction flask and stirred for 10 minutes. Acetic anhydride (0.91 mL) was added and the reaction mixture was stirred at 80° C. for 1 hour. The quinoline from Step 3 of Part A(2 g) was added to the reaction flask and the reaction mixture was refluxed for 24 hours. Following evaporation of the solvent, the residue was purified via flash column separation. A NMR spectrum showed the product to have a structure consistent with 5-ethoxy-2,2-diphenyl-2H-pyrano[3,2-c]quinoline.

EXAMPLE 4

The procedure of Example 3 was followed except that 4-methoxy aniline (40 g) was used in place of aniline in Step 2 of Part A. An NMR spectrum showed the final product to have a structure consistent with 5-ethoxy-9-methoxy-2,2-diphenyl-2H-pyrano[3,2-c]quinoline.

EXAMPLE 5

The procedure of Example 3 was followed except that 2-methoxy aniline (40 g) was used in place of aniline in Step 2 of Part A. An NMR spectrum showed the final product to have a structure consistent with 5-ethoxy-7-methoxy-2,2-diphenyl-2H-pyrano[3,2-c]quinoline.

EXAMPLE 6

The procedure of Example 3 was followed except that 2-aminonapthalene (47 g) was used in place of aniline in Step 2 of Part A. An NMR spectrum showed the final product to have a structure consistent with 12-ethoxy-3,3-diphenyl-3H-benzo[h]pyrano[3,2-c] quinoline.

EXAMPLE 7

The procedure of Example 3 was followed except that 2,4-dimethoxy aniline (51 g) was used in place of aniline in Step 2 of Part A. An NMR spectrum showed the final product to have a structure consistent with 5-ethoxy-7,9-dimethoxy-2,2-diphenyl-2H-pyrano[3,2-c)quinoline.

EXAMPLE 8

The procedure of Example 3 was followed except that 4-fluoro aniline (36 g) was used in place of aniline in Step 2 of Part A. An NMR spectrum showed the final product to have a structure consistent with 5-ethoxy-9-fluoro-2,2-diphenyl-2H-pyrano[3,2-c]quinoline.

EXAMPLE 9

The procedure of Example 3 was followed except that 2-fluoro aniline (36 g) was used in place of aniline in Step 2 of Part A. An NMR spectrum showed the final product to have a structure consistent with 5-ethoxy-7-fluoro-2,2-diphenyl-2H-pyrano[3,2-c]quinoline.

EXAMPLE 10

Part A

The procedure of Example 3, Part A was followed except that 4-methoxy aniline (41 g) was used in place of aniline to produce 2-ethoxy-6-methoxy-quinol-4-ol.

Part B

Step 1

1,3-Dimethoxybenzene (13.8 g) and p-anisoyl chloride (17 g) were dissolved in a reaction flask containing 200 mL of methylene chloride and stirred at room temperature. Anhydrous aluminum chloride (15 g) was added slowly to the reaction mixture over a period of 15 minutes with stirring. After stirring an additional 15 minutes, the contents of the flask were carefully poured into 200 mL of a mixture of ice and dilute hydrochloric acid. The organic fraction was separated and washed with water. The solvent was removed on a rotary evaporator leaving an oily product that solidified on standing. This solid was broken-up, washed with two 50 mL ortions of pentane, and dried, yielding (2,4-dimethoxy-phenyl)-(4-methoxy-phenyl)-methanone.

Part B

Step 2

2,4,4,6-Tetramethyl-5,6-dihydro-1,3-oxazine (14.1 g) was added to a reaction flask containing anhydrous THF (100 mL). The stirred solution was cooled to −78° C. and n-butyllithium (0.11 mole) in hexane was added. After 2 hours, 27 g of the (2,4-dimethoxy-phenyl)-(4-methoxy-phenyl)-methanone produced in Step 1 of this Part B in 30 mL of anhydrous THF was added into the mixture over a period of 30 minutes. The reaction mixture was allowed to slowly ambient temperature for 2 hours. The mixture was then poured into 100 mL of ice water and acidified with concentrated HCl. The acidic solution was extracted with hexane and made basic by the addition of 40% NaOH solution. The resulting oil was extracted with ether, dried, and evaporated to produce a dihydrooxazine which was not purified but used directly in the next step.

Part B

Step 3

The dihydrooxazine (15 g) obtained in Step 2 of this Part B was added to a reaction flask containing 100 mL THF and 100 mL ethanol. The mixture was cooled to −40° C. and concentrated HCl was added until an approximate pH of 7 was obtained. A sodium borohydride solution and concentrated HCl were added to the stirred solution alternately to maintain a pH of 6–8. After the addition was completed, the solution was stirred for 1 hour at room temperature. The mixture was poured into 100 mL of water and made basic by addition of 40% NaOH solution. The resulting layers were separated, and the aqueous solution was extracted with ether and dried over anhydrous potassium carbonate. After evaporation, a tetrahydrooxazine was obtained which was not purified but used directly in the next step.

Part B

Step 4

The tetrahydrooxazine (0.1 mole) from Step 3 of this Part B and oxalic acid (50.4 g, 0.4 mole) were added to a flask containing 150 mL of water. The mixture was refluxed for 2 hours and cooled to room temperature. The reaction mixture was washed with 5% sodium bicarbonate solution, dried, and recrystallized from dichloromethane/hexane a 80:20 volume ratio to give pure a light yellow crystal. An NMR spectrum showed the final product to have a structure consistent with 1-(2,4-dimethoxy-phenyl)-1-(4-methoxy-phenyl)-prop-2-yn-1-ol.

Part C

The 1-(2,4-dimethoxy-phenyl)-1-(4-methoxy-phenyl)-prop-2-yn-1-ol from Step 3 of this Part B (2.6 g) was dissolved in 20 mL of toluene in a reaction flask at 0° C. Piperidine (0.82 g) was added to the reaction flask and stirred for 10 minutes. Acetic anhydride (0.91 mL) was added and the reaction mixture was stirred at 80° C. for 1 hour. The 2-ethoxy-6-methoxy-quinolin-4-ol (2 g) produced in Part A of this example was added to the reaction flask, and the reaction mixture was refluxed for 24 hours. Following evaporation of the solvent, the residue was purified via flash column separation. A NMR spectrum showed the product to have a structure consistent with 2-(2,4-dimethoxy-phenyl)-5-ethoxy-9-methoxy-2-(4-methoxy-phenyl)-2H-pyrano[3,2-c]quinoline.

EXAMPLE 11

The procedure of Example 10 was followed except as follows. In Part A, 1-amino napthalene (47 g) was used in place of 4-methoxy aniline. In Step 1 of Part B, 2-fluorobenzoyl chloride (15.8 g) and anisole (10.8 g) were used in place of 1,3-dimethoxybenezene and p-anisoyl chloride respectively to produce (2-fluoro-phenyl)-(4-methoxy-phenyl)-methanone. An NMR spectrum showed the final product to have a structure consistent with 12-ethoxy-3-(2-fluorophenyl)-3-(4-methoxy)-3H-benzo[h]pyrano[3,2-c]quinoline.

EXAMPLE 12

The procedure of Example 11 was followed except that 4-methoxy aniline (40 g) was used in place of 1-amino napthalene. An NMR spectrum showed the final product to have a structure consistent with 5-ethoxy-2-(2-fluorophenyl)-9-methoxy-2-(4-methoxyphenyl)-2H-pyrano[3,2-c]quinoline.

EXAMPLE 13

The procedure of Example 11 was followed except that 3,4-methylenedioxy aniline (45 g) was used in place of 1-amino napthalene. An NMR spectrum showed the final product to have a structure consistent with 5-ethoxy-3-(2-fluorophenyl)-3-(4-methoxy)-2H-[1,3]-dioxolo[4.5-g]pyrano[3,2-c]quinoline.

EXAMPLE 14

Step 1

A reaction flask was. charged with 10 g of (2,4-dimethoxy-phenyl)-(4-methoxy-phenyl)-methanone as prepared in Step 1 of Part B of Example 10, 150 mL of tetrahydrofuran, and 14.0 g of 18 weight percent slurry of sodium acetylide in xylene/mineral oil. The reaction mixture was stirred at room temperature under a nitrogen atmosphere for 24 hours. The contents of the flask were poured into a 500 mL beaker containing ice water and extracted three times with 100 mL portions of methylene chloride. The extracts were combined, dried over anhydrous magnesium sulfate and the solvent was removed under vacuum. The product was shown by NMR to have a structure consistent with 1-(2, 4-dimethoxy-phenyl)-1(4-methoxy)-2-propyn-1-ol.

Step 2

2-Ethoxy-benzo[h]quinolin-4-ol (2 g), an intermediate of the procedure of Example 6, and 2.5 g of the 1-(2,4-dimethoxy-phenyl)-1-(4-methoxy-phenyl)-2-propyn-1-ol (2.5 g) from Step 1 were added to a reaction flask containing 100 mL chloroform and stirred at room temperature under nitrogen. A few drops of boron trifluoride in ether were added to the reaction mixture and stirred for 24 hours. The solvent was evaporated and recrystallized from dichloromethane/hexane in a 80:20 volume ratio to give a product having an NMR spectrum consistent with the structure of 12-ethoxy-3-(2,4-dimethoxy-phenyl)-3-(4-methoxyphenyl)-3H-benzo[h]pyrano(3,2-c]quinoline.

EXAMPLE 15

β-Phenylcinnamaldehyde (5.9 g), anhydrous $MgSO_4$ (10 g) and 30 mL of pyridine were added to a reaction flask and heated until boiling with stirring. A solution of 4-hydroxy-1-methyl-2(1H)-quinolone (5.0g) in 30 mL of pyridine was added to the boiling mixture over a 60 minute time interval while stirring. The resulting mixture was stirred and refluxed for another 15 minutes and the pyridine was evaporated. Water and ether were added and the ethereal solution was extracted with dilute acid followed by a extraction with a dilute $NaHCO_3$ solution. Following evaporation of the solvent, the residue was purified via flash column separation. A nuclear magnetic resonance (NMR) spectrum showed the product to have a structure consistent with 2,2-diphenyl-6-methyl-5,6-dihydro-2H-pyrano[3,2-c]quinolin-5-one.

EXAMPLE 16

The Photochromic Performance Test comprises the preparation of photochromic polymeric test samples using the Examples of the present invention in Part A and testing the photochromic performance as described in Part B.

Part A

Preparation of test samples was done with the photochromic compounds described in Examples 1 through 15. For the test squares of Examples 2–14, a quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). For the test squares of Examples 1 and 15, the quantity of photochromic compound used was 25 percent and 50 percent, respectively, of the amount used for Examples 2–14. For each test square, the photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour period hold the temperature at 95° C. for 3 hours, lower it to 60° C. over a 2 hour interval and then hold it at 60° C. for up to 6 hours. After the mold was opened, the polymer sheet was cut using a diamond blade saw into 2 inch (5.1 centimeters) test squares.

Part B

The photochromic test squares prepared in Part A were tested for photochromic response on Optical Bench A or B as described hereinbelow. The optical benches were maintained at a temperature of 72° F. (22° C.)

Prior to testing on the optical benches, the photochromic test squares were exposed to 365 nm ultraviolet light for about 15 minutes at a distance of about 6 inches (15 cm) from the lamps to activate the photochromic compound. The samples were then placed in an oven at 75° C. for 15 minutes to bleach, or inactivate, the photochromic compound in the samples. The test squares were then cooled to room temperature, while exposed to fluorescent room lighting, approximately 1000 Lux for at least 2 hours and then kept covered at room temperature for another 2 hours prior to testing on the optical benches.

Optical Bench A was used for the test squares of Examples 1 through 7, 13 and 15. It was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from about 1.4 to 1.9 Watts per square meter ($W/m^2$). Measurement of the power output was made using a GRASEBY Optronics Model S-371 portable photometer (Serial #21536) with a Lw-A detector (Serial #22411) or comparable equipment. The Lw-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 300) normal to the square. After passing through the square, the light from the tungsten lamp was directed to a detector through a Spectral Energy Corp. GM-200 monochromator set at the previously determined visible lambda max of the photochromic compound being measured. For the test squares of Examples 1 and 15 the visible lambda max was set at 450 nanometers (nm). The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state after 15 minutes, and calculating the change in optical density according to the formula: $\Delta OD=\log(100/\% Ta)$, where % Ta is the percent transmittance in the activated state and the logarithm is to the base 10. LABTECH NOTEBOOKpro software was used for all calculations.

The performance properties of the photochromic compounds in the test squares of Examples 1 through 7, 13 and 15 are reported in Table 1.

Optical Bench B was used for the test squares of Examples 8 through 12 and 14. It comprised a rail to which was fitted a 300 watt Xenon arc lamp, a remote controlled shutter, a Schott 3mm KG-2 band-pass filter, which removed short wavelength radiation, neutral density filter(s), a quartz water cell/sample holder for maintaining sample temperature in which the test sample to be tested was inserted.

Measurements were made on Optical Bench B with the power output adjusted to 3.0 Watts per square meter. Measurement of the power output was made using an International Light Research Radiometer (Model #: IL1700; Serial #: 1290) with a radiometer detector (Model #: SED 033; Serial #: 5886) or comparable equipment. The radiometer was placed in an optical rail carrier on the rail at the correct focal length and the light output was measured. Adjustments to the power output were made by increasing or decreasing the lamp wattage or by adding or removing neutral density filters in the light path.

The test squares of Examples 8–12 and 14 were exposed to UV irradiation using a Xenon arc lamp at 300 normal to the surface of the test square. A monitoring, collimated beam of light from the tungsten/halogen lamp maintained perpendicular to the test sample was passed through it and then directly into an integrating sphere attached to a spectrophotometer. The integrating sphere is a device to collect and mix all of monitoring light that passes through the test sample. The control of the test conditions and acquisition of the data was handled by a proprietary program in conjunction with OOI Base 32 software provided by Ocean Optics, Inc.

The change in optical density ($\Delta OD$) of the test squares tested on Optical Bench B were determined using a similar procedure as done on Optical Bench A. The results of the Photochromic Performance Test on test squares of Examples 8–12 and 14 are included in Table 1.

The Fade Half Life (T ½) was determined on the respective optical benches used for testing the test squares of the examples. Fade Half Life is the time interval in seconds for the $\Delta OD$ of the activated form of the photochromic compound in the test square to reach one half the highest $\Delta OD$ measured after fifteen minutes of activation at 72° F. (22° C.), after removal of the source of activating light, e.g., by closing the shutter.

A Varian Cary 3 UV-Visible spectrophotometer or a comparable instrument was used to determine the lambda max values. The lambda max in the ultraviolet range ($\lambda$max (UV)) is the wavelength in the ultraviolet range closest to the visible spectrum at which the absorption of the photochromic compound occurs. The lambda max in the visible light range ($\lambda$max (Vis)) is the wavelength in the visible spectrum at which the maximum absorption of the activated form of the photochromic compound occurs. The lambda max values for the test squares of Examples 1–15 are included in Table 1.

TABLE 1

| Example No. | λ max (UV) | λ max (Vis) | ΔOD after 15 minutes | T ½ (seconds) |
| --- | --- | --- | --- | --- |
| 1* | 417 | 417 | 0.23 | 99 |
| 2* | 341 | 415 | 0.33 | 156 |
| 3* | 342 | 409 | 0.04 | 35 |
| 4* | 362 | 415 | 0.15 | 28 |
| 5* | 322 | 440 | 0.05 | 24 |
| 6* | 371 | 428 | 0.06 | 8 |
| 7* | 336 | 419 | 0.17 | 32 |
| 8** | 343 | 413 | 0.08 | 46 |
| 9** | 323 | 413 | 0.04 | 34 |
| 10** | 348 | 474 | 0.99 | 306 |
| 11** | 365 | 465 | 0.32 | 67 |
| 12** | 321 | 449 | 0.74 | 184 |
| 13* | 334 | 454 | 0.16 | 143 |
| 14** | 369 | 479 | 0.32 | 174 |
| 15* | 376 | 417 | 0.37 | 79 |

*Tested according to the procedures used for Optical Bench A.
**Tested according to the procedures used for Optical Bench B.

The results of Table 1 show that a range of values for the lambda max (visible and ultraviolet) $\Delta OD$ at Saturation after 15 minutes and Fade Half-life (T½) are obtained for the Example Compounds 1 through 15 of the present invention depending on the nature of the substituents at the 2-, 5-, 6-, 7-, 8-, 9-, and/or 10-position carbon ring atoms. It is believed that the lambda max (visible and ultraviolet) results for Example 1 are the same due to the presence of the tautomeric isomers in the sample.

The present invention has been described with reference to specific details of particular embodiments thereof. It is not intended that such details be regarded as limitations upon the scope of the invention except insofar as to the extent that they are included in the accompanying claims.

We claim:

1. A composition comprising at least one material represented by at least one of the following graphic formulae or mixtures thereof:

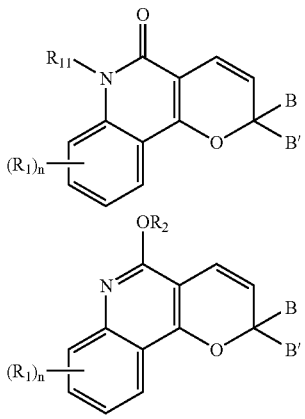

wherein:
- (a) $R_{11}$ is chosen from hydrogen, $C_1$–$C_{12}$ alkyl, $C_1$–$C_{12}$ acyl, phenyl($C_1$–$C_{12}$)alkyl, $C_1$–$C_{12}$ alkoxy($C_1$–$C_{12}$) alkyl or —CH($R_3$)Q, wherein $R_3$ being chosen from hydrogen or $C_1$–$C_{12}$ alkyl and Q is —COOR$_4$ and $R_4$ is $C_1$–$C_{12}$ alkyl;
- (b) $R_1$ is independently chosen for each occurrence from:
  - (i) hydrogen, hydroxy, $C_1$–$C_{12}$ alkyl, vinyl, $C_3$–$C_7$ cycloalkyl, $C_1$–$C_{12}$ haloalkyl, allyl, benzyl or monosubstituted benzyl; each of said benzyl substituents being $C_1$–$C_{12}$ alkyl or $C_1$–$C_{12}$ alkoxy;
  - (ii) phenyl or mono-substituted phenyl; each of said phenyl substituents in (ii) being chosen independently for each occurrence from chloro, fluoro, $C_1$–$C_{12}$ alkyl or $C_1$–$C_{12}$ alkoxy;
  - (iii) a mono-substituted phenyl, said phenyl having a substituent located at the para position being —O—(CH$_2$)$_t$—, wherein t is chosen from the integer 1, 2, 3 or 4, said substituent being connected to an aryl group on another photochromic material;
  - (iv) —OR$_2$, $R_2$ being chosen from $R_{11}$;
  - (v) —CH(Q')$_2$, Q' is —COOR$_6$ and $R_6$ is $C_1$–$C_{12}$ alkyl;
  - (vi) —OH(R$_7$)G, $R_7$ is hydrogen or $C_1$–$C_{12}$ alkyl, and G is —COOR$_5$ or —CH$_2$OR$_9$, wherein $R_8$ is $C_1$–$C_{12}$ alkyl and $R_9$ is $C_1$–$C_{12}$ alkyl or $C_1$–$C_{12}$ alkoxy($C_1$–$C_{12}$)alkyl;
  - (vii) the group T represented by the formula:

wherein -Z is —CH$_2$-, Z' is $C_1$–$C_{12}$ alkoxy or a polymerizable group, x, y and z are each an number between 0 and 20, and the sum of x, y and z is between 2 and 20;

- (viii) —SR$_{10}$, $R_{10}$ is $C_1$–$C_{12}$ alkyl;
- (ix) —N(R$_{11}$)R$_{12}$, $R_{12}$ is the same as $R_{11}$ described herein before;
- (x) a nitrogen containing ring represented by the following graphic formula IIA:

wherein each Y being independently chosen for each occurrence from —CH$_2$— or —CH(R$_{13}$)—; X being —Y—, —O—, —S—, —NH—, —NR$_{13}$— or —N—aryl; $R_{13}$ being $C_1$–$C_{12}$ alkyl; m is the integer 1, 2 or 3 and p is an integer chosen from 0, 1, 2 or 3; provided that when p is 0, X is Y;
- (xi) a group represented by one of the following graphic formulae IIB or IIC:

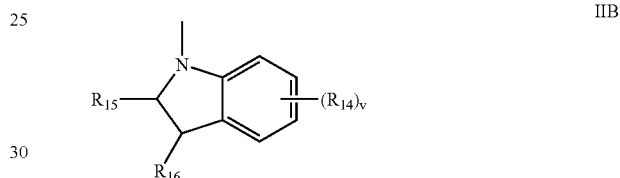

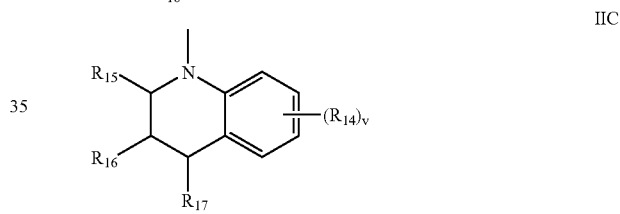

wherein $R_{15}$, $R_{16}$ and $R_{17}$ are each independently chosen for each occurrence in each formula from hydrogen or $C_1$–$C_{12}$ alkyl, $R_{14}$ is independently chosen for each occurrence from $C_1$–$C_{12}$ alkyl, $C_1$–$C_{12}$ alkoxy, fluoro or chloro and v being chosen from the integer 0, 1 or 2; or
- (xii) adjacent $R_1$ substituents come together to form one of the following graphic formulae IID or IIF:

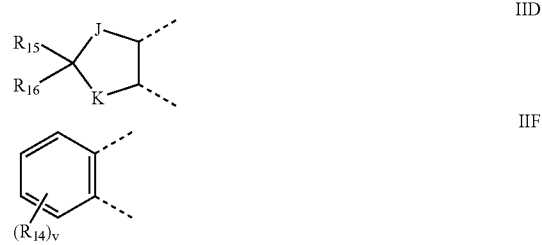

wherein J and K being independently chosen for each occurrence in each formula from oxygen or —NR$_{11}$—, wherein $R_{11}$, $R_{14}$, $R_{15}$ and $R_{16}$ each being the same as described herein before;
- (c) $R_2$ is chosen from $R_{11}$; and
- (d) B and B' are each chosen from:

(i) phenyl, mono- and di-substituted phenyl;
(ii) the unsubstituted, mono- and di-substituted heteroaromatic groups furanyl, benzofuran-2-yl, thienyl and benzothien-2-yl, each of said phenyl and heteroaromatic substituents in (i) and (ii) being chosen from $C_1$–$C_{12}$ alkyl, $C_1$–$C_{12}$ alkoxy and fluoro; or
(iii) the group represented by graphic formula IIG, wherein A is carbon and D is oxygen, $R_{19}$ is $C_1$–$C_{12}$ alkyl or $C_1$–$C_{12}$ alkoxy, $R_{17}$ and $R_{18}$ are each hydrogen or $C_1$–$C_{12}$ alkyl, and q is the integer 0 or 1.

2. The composition of claim 1 wherein the at least one material is a photochromic material chosen from:
   (a) a single photochromic compound;
   (b) a mixture of photochromic compounds;
   (c) a material comprising at least one photochromic compound;
   (d) a material to which at least one photochromic compound is chemically bonded;
   (e) said material (c) or (d) further comprising an encapsulating coating;
   (f) a photochromic polymer; or
   (g) mixtures thereof.

3. A composition comprising an isomeric mixture of materials represented by the following graphic formulae:

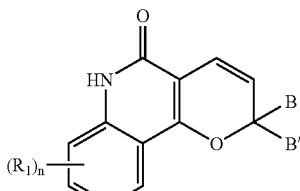

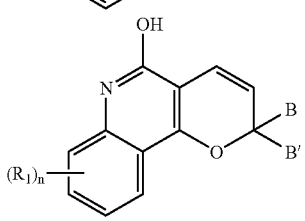

wherein:
(a) each $R_1$ is independently chosen from:
   (i) hydrogen, hydroxy, $C_1$–$C_{12}$ alkyl, $C_2$–$C_{12}$ alkylidence, $C_2$–$C_{12}$ alkylidyne, vinyl, $C_3$–$C_7$ cycloalkyl, $C_1$–$C_{12}$ haloalkyl, allyl, benzyl, mono-substituted benzyl, halogen or the group, —C(O)W, wherein W being hydroxy, $C_1$–$C_{12}$ alkyl, $C_1$–$C_{12}$ alkoxy, phenyl, mono-substituted phenyl, amino, mono($C_1$–$C_{12}$)alkylamino, di($C_1$–$C_{12}$)alkylamino; said amino substituents being $C_1$–$C_{12}$ alkyl, phenyl, benzyl or naphthyl; each of said benzyl and phenyl substituents being $C_1$–$C_{12}$ alkyl or $C_1$–$C_{12}$ alkoxy:
   (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (ii) being chosen independently for each occurrence from halogen, $C_1$–$C_{12}$ alkyl or $C_1$–$C_{12}$ alkoxy;
   (iii) a mono-substituted phenyl, said phenyl having a substituent located at the para position being —($CH_2$)$_t$— or —O—($CH_2$)$_t$—, wherein t is an integer chosen from 1, 2, 3, 4, 5 or 6; said substituent being connected to an aryl group on another photochromic material;
   (iv) —$OR_2$, $R_2$ being chosen from
      (a') hydrogen, $C_1$–$C_{12}$ alkyl, $C_1$–$C_{12}$ acyl, phenyl($C_1$–$C_{12}$)alkyl, mono($C_1$–$C_{12}$)alkyl substituted phenyl($C_1$–$C_{12}$)alkyl, mono($C_1$–$C_{12}$)alkoxy substituted phenyl($C_1$–$C_{12}$)alkyl, $C_1$–$C_{12}$ alkoxy($C_1$–$C_{12}$)alkyl, $C_3$–$C_7$ cycloalkyl, mono($C_1$–$C_{12}$)alkyl substituted $C_3$–$C_7$ cycloalkyl, $C_1$–$C_{12}$ haloalkyl, allyl, benzoyl, mono-substituted benzoyl, naphthoyl or mono-substituted naphthoyl; each of said benzoyl and naphthoyl substituents being independently chosen from $C_1$–$C_{12}$ alkyl or $C_1$–$C_{12}$ alkoxy;
      (b') —$CH(R_3)Q$, wherein $R_3$ being chosen from hydrogen or $C_1$–$C_{12}$ alkyl and Q being chosen from —CN, —$CF_3$, or —$COOR_4$ and $R_4$ being chosen from hydrogen or $C_1$–$C_{12}$ alkyl;
      (c') —C(O)V, wherein V being chosen from hydrogen, $C_1$–$C_{12}$ alkoxy, phenoxy, mono- or di-($C_1$–$C_{12}$)alkyl substituted phenoxy, mono- or di-($C_1$–$C_{12}$)alkoxy substituted phenoxy, an unsubstituted, mono- or di-substituted aryl group, amino, mono($C_1$–$C_{12}$)alkylamino, di($C_1$–$C_{12}$)alkylamino, phenylamino, mono- or di-($C_1$–$C_{12}$)alkyl substituted phenylamino, or mono- or di-($C_1$–$C_{12}$)alkoxy substituted phenylamino; each of said aryl group substituents being independently chosen from $C_1$–$C_{12}$ alkyl or $C_1$–$C_{12}$ alkoxy; or
      (d') tri($C_1$–$C_{12}$)alkylsilyl, tri($C_1$–$C_{12}$)alkoxysilyl, di($C_1$–$C_{12}$)alkyl ($C_1$–$C_{12}$ alkoxy)silyl or di($C_1$–$C_{12}$)alkoxy($C_1$–$C_{12}$ alkyl)silyl;
   (v) —$CH(Q')_2$, Q' being chosen from —CN or $COOR_6$ and $R_6$ being chosen from hydrogen, $C_1$–$C_{12}$ alkyl, phenyl($C_1$–$C_{12}$)alkyl, mono($C_1$–$C_{12}$)alkyl substituted phenyl($C_1$–$C_{12}$)alkyl, mono($C_1$–$C_{12}$)alkoxy substituted phenyl($C_1$–$C_{12}$)alkyl or an unsubstituted, mono- or di-substituted aryl group; each of said aryl group substituents being independently chosen from $C_1$–$C_{12}$ alkyl or $C_1$–$C_{12}$ alkoxy;
   (vi) —$CH(R_7)G$, $R_7$ being chosen from hydrogen, $C_1$–$C_{12}$ alkyl or an unsubstituted, mono- or di-substituted aryl group and G being chosen from —$COOR_5$, —$COR_8$ or —$CH_2OR_9$; wherein $R_8$ being chosen from hydrogen, $C_1$–$C_{12}$ alkyl, an unsubstituted, mono- or di-substituted aryl group, amino, mono($C_1$–$C_{12}$)alkylamino, di($C_1$–$C_{12}$)alkylamino, phenylamino, mono- or di-($C_1$–$C_{12}$)alkyl substituted phenylamino, mono- or di-($C_1$–$C_{12}$) alkoxy substituted phenylamino, diphenylamino, mono- or di-($C_1$–$C_{12}$)alkyl substituted diphenylamino, mono- or di-($C_1$–$C_{12}$)alkoxy substituted diphenylamino, morpholino or piperidino $R_9$ being chosen from hydrogen, —C(O)$R_6$, $C_1$–$C_{12}$ alkyl, $C_1$–$C_{12}$ alkoxy($C_1$–$C_{12}$)alkyl, phenyl($C_1$–$C_{12}$)alkyl, mono($C_1$–$C_{12}$)alkoxy substituted phenyl($C_1$–$C_{12}$) alkyl or an unsubstituted, mono- or di-substituted aryl group, each of said aryl group substituents being independently chosen from $C_1$–$C_{12}$ alkyl or $C_1$–$C_{12}$ alkoxy;
   (vii) the group T represented by the formula:

wherein -Z is chosen from —C(O)— or —CH₂—, Z' being chosen from C₁–C₁₂ alkoxy or a polymerizable group, x, y and z are each an number between 0 and 50, and the sum of x, y and z is between 2 and 50;

(viii) —SR₁₀, R₁₀ being chosen from C₁–C₁₂ alkyl, aryl, mono- or di-substituted aryl, and each of said aryl substituents being chosen independently from C₁–C₁₂ alkyl, C₁–C₁₂ alkoxy or halogen;

(ix) —N(R₁₁)R₁₂, wherein R₁₁ and R₁₂ are the same as R₂ described hereinbefore at (a)(iv)(a'), (a)(iv)(b') and (a)(iv)(c');

(x) a nitrogen containing ring represented by the following graphic formula IIA:

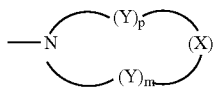

IIA wherein each Y being independently chosen for each occurrence from —CH₂—, —CH(R₁₃)—, —C(R₁₃)(R₁₃)—, —CH(aryl)—, —CH(aryl)₂— or —C(R₁₃)(aryl)—; X being —Y—, —O—, —S—, —S(O)—, —S(O₂)—, —NH—, —NR₁₃— or —N—aryl; R₁₃ being C₁–C₁₂ alkyl; said aryl group being phenyl or naphthyl, m is an integer chosen from 1, 2 or 3 and p is an integer chosen from 0, 1, 2 or 3; provided that when p is 0, X is Y;

(xi) a group represented by one of the following graphic formulae IIB or IIC:

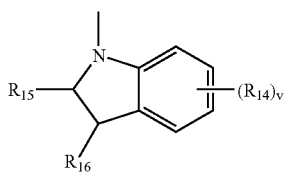

IIB

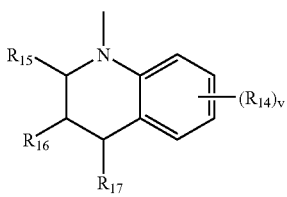

IIC wherein R₁₅, R₁₆ and R₁₇ are each chosen independently for each occurrence in each formula from hydrogen, C₁–C₁₂ alkyl, phenyl or naphthyl; or the groups R₁₅ and R₁₆ together form a ring of 5 to 8 carbon atoms, R₁₄ being chosen independently for each occurrence from C₁–C₁₂ alkyl, C₁–C₁₂ alkoxy, or halogen and v is an integer chosen from 0, 1 or 2;

(xii) unsubstituted, mono- or di- substituted C₄–C₁₈ spirobicyclic amine;

(xiii) unsubstituted, mono- or di-substituted C₄–C₁₈ spirotricyclic amine; said substituents for (xii) and (xiii) being independently chosen for each occurrence from aryl, C₁–C₁₂ alkyl, C₁–C₁₂ alkoxy or phenyl (C₁–C₁₂) alkyl; or (xiv) adjacent R₁ substituents come together to form one of the following graphic formulae IID, IIE, or IIF;

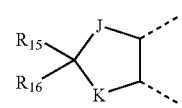

IID

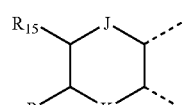

IIE

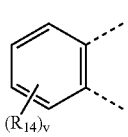

IIF wherein J and K being independently chosen for each occurrence in each formula from oxygen or —NR₁₁—, R₁₁, R₁₄, R₁₅ and R₁₆ each being the same as described herein before, and n is an integer chosen from 0, 1, 2, 3 or 4; and (b) B and B' are each independently chosen from:

(i) mono-T-substituted phenyl wherein the group T is represented by the formula:

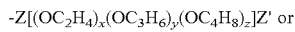

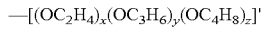

wherein -Z is —C(O)— or —CH₂, Z' is C₁–C₁₂ alkoxy or a polymerizable group, x, y and z are each an number between 0 and 50, and the sum of x, y and z is between 2 and 50;

(ii) an unsubstituted, mono-, di-, or tri-substituted aryl group;

(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopynidyl, indolinyl or fluorenyl, each of said aryl and heteroaromatic substituents in (ii) and (iii) being independently chosen from hydroxy, the group, —C(O)W, defined hereinbefore, aryl, mono(C₁–C₁₂)alkoxyaryl, di(C₁–C₁₂)alkoxyaryl, mono(C₁–C₁₂)alkylaryl, di(C₁–C₁₂)alkylaryl, haloaryl, C₃–C₇ cycloalkylaryl, C₃–C₇ cycloalkyl, C₃–C₇ cycloalkyloxy, C₃–C₇ cycloalkyloxy(C₁–C₁₂)alkyl, C₃–C₇ cycloalkyloxy(C₁–C₁₂)alkoxy, aryl(C₁–C₁₂)alkyl, aryl(C₁–C₁₂)alkoxy, aryloxy, aryloxy(C₁–C₁₂)alkyl, aryloxy(C₁–C₁₂)alkoxy, mono- or di-(C₁–C₁₂)alkylaryl(C₁–C₁₂)alkyl, mono- or di-(C₁–C₁₂)alkoxyaryl (C₁–C₁₂)alkyl, mono- or di-(C₁–C₁₂)alkylaryl (C₁–C₁₂)alkoxy, mono- or di-(C₁–C₁₂)alkoxyaryl (C₁–C₁₂)alkoxy, amino, mono(C₁–C₁₂)alkylamino, di(C₁–C₁₂)alkylamino, diarylamino, piperazino, N-(C₁–C₁₂)alkylpiperazino, N-arylpiperazino, aziridino, indolino, piperidino, morpholino, thiomorpholino, tetrahydroquinolino, tetrahydroisoquinolino, pyrrolidyl, C₁–C₁₂ alkyl, C₁–C₁₂ haloalkyl, C₁–C₁₂ alkoxy, mono(C₁–C₁₂)alkoxy(C₁–C₁₂)alkyl, acryloxy, methacryloxy, or halogen;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$–$C_{12}$ alkyl, $C_1$–$C_{12}$ alkoxy, phenyl, or halogen;
(v) a monosubstituted phenyl, said phenyl having a substituent located at the para position being —$(CH_2)_t$— or —O—$(CH_2)_t$—, wherein t is chosen from the integer 1, 2, 3, 4, 5 or 6, said substituent being connected to an aryl group on another photochromic material;
(vi) a group represented by one of the following graphic formulae IIG or IIH:

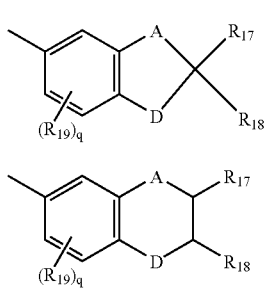

wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$–$C_{12}$ alkyl, or $C_2$–$C_{12}$ acyl; each $R_{19}$ being independently chosen for each occurrence in each formula from $C_1$–$C_{12}$ alkyl, $C_1$–$C_{12}$ alkoxy, hydroxy, or halogen; $R_{17}$ and $R_{18}$ each being independently chosen in each formula from hydrogen or $C_1$–$C_{12}$ alkyl; and q being chosen from the integer 0, 1 or 2;
(vii) $C_1$–$C_{12}$ alkyl, $C_1$–$C_{12}$ haloalkyl, $C_1$–$C_{12}$ alkoxy $(C_1$–$C_{12})$alkyl, $C_3$–$C_7$ cycloalkyl, mono$(C_1$–$C_{12})$ alkoxy $(C_3$–$C_7)$cycloalkyl, mono$(C_1$–$C_{12})$alkyl $(C_3$–$C_7)$-cycloalkyl, halo$(C_3$–$C_7)$cycloalkyl, or $C_4$–$C_{12}$ bicycloalkyl, provided that both B and B' are not chosen from (vii):
(viii) a group represented by the following graphic formula IIJ:

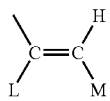

wherein L being chosen from hydrogen or $C_1$–$C_{12}$ alkyl and M being chosen from an unsubstituted, mono-, or di-substituted group chosen from naphthyl, phenyl, furanyl, or thienyl; each of said group substituents being independently chosen from $C_1$–$C_{12}$ alkyl, $C_1$–$C_{12}$ alkoxy, or halogen; or
(ix) B and B' taken together form a fluoren-9-ylidene, mono-, or di- substituted fluoren-9-ylidene or a spirocyclic group chosen from saturated $C_3$–$C_{12}$ spiro-monocyclic hydrocarbon rings, saturated $C_7$–$C_{12}$ spiro-bicyclic hydrocarbon rings, or saturated $C_7$–$C_{12}$ spiro-tricyclic hydrocarbon rings, provided that said spirocyclic group is not norbornylidene or bicyclor[3.3.1]9-nonylidene, each of said fluoren-9-ylidene substituents being independently chosen from $C_1$–$C_{12}$ alkyl, $C_1$–$C_{12}$ alkoxy or halogen.

4. The composition of claim 3 wherein the isomeric mixture of materials comprises a mixture of:
(a) 2,2-diphenyl-2H-pyrano[3,2-c]quinolin-5-ol; and
(b) 2,2-diphenyl-5,6-dihydro-2H-pyrano[3,2-c]quinolin-5-one.

5. A photochromic composition comprising at least one compound chosen from:
(a) 5-methoxy-2,2-diphenyl-2H-pyrano[3,2-c]quinoline;
(b) 5-ethoxy-2,2-diphenyl-2H-pyrano[3,2-c]quinoline;
(c) 5-ethoxy-9-methoxy-2,2-diphenyl-2H-pyrano[3,2-c]quinoline;
(d) 5-ethoxy-7-methoxy-2,2-diphenyl-2H-pyrano[3,2-c]quinoline;
(e) 12-ethoxy-3,3-diphenyl-3H-benzo[h]pyrano[3,2-c]quinoline;
(f) 5-ethoxy-7,9-dimethoxy-2,2-diphenyl-2H-pyrano[3,2-c]quinoline;
(g) 5-ethoxy-9-fluoro-2,2-diphenyl-2H-pyrano[3,2-c]quinoline;
(h) 5-ethoxy-7-fluoro-2,2-diphenyl-2H-pyrano[3,2-c]quinoline;
(i) 2-(2,4-dimethoxyphenyl)-5-ethoxy-9-methoxy-2-(4-methoxyphenyl)-2H-pyrano[3,2-c]quinoline;
(j) 12-ethoxy-3-(2-fluorophenyl)-3-(4-methoxy)-3H-benzo[h]pyrano[3,2-c]quinoline;
(k) 5-ethoxy-2-(2-fluorophenyl)-9-methoxy-2-(4-methoxyphenyl)-2H-pyrano[3,2-c]quinoline;
(l) 5-ethoxy-3-(2-fluorophenyl)-3-(4-methoxy)-2H-[1,3]-dioxolo[4,5-g]pyrano[3,2-c]quinoline;
(m) 12-ethoxy-3-(2,4-dimethoxyphenyl)-3-(4-methoxyphenyl)- 3H-benzo[h]pyrano[3,2-c]quinoline;
(n) 2,2-diphenyl-6-methyl-5,6-dihydro-2H-pyrano[3,2-c]quinolin-5-one; or
(p) mixtures thereof.

* * * * *